United States Patent
Sills et al.

(10) Patent No.: US 10,768,708 B1
(45) Date of Patent: Sep. 8, 2020

(54) SYSTEMS AND METHODS OF INTERACTING WITH A ROBOTIC TOOL USING FREE-FORM GESTURES

(71) Applicant: Ultrahaptics IP Two Limited, Bristol (GB)

(72) Inventors: Maxwell Sills, San Francisco, CA (US); Robert S. Gordon, San Francisco, CA (US); Paul Durdik, Foster City, CA (US)

(73) Assignee: Ultrahaptics IP Two Limited, Bristol (GB)

( * ) Notice: Subject to any disclaimer, the term of this patent is extended or adjusted under 35 U.S.C. 154(b) by 34 days.

(21) Appl. No.: 14/833,016

(22) Filed: Aug. 21, 2015

Related U.S. Application Data

(60) Provisional application No. 62/040,169, filed on Aug. 21, 2014.

(51) Int. Cl.
| | |
|---|---|
| *G06F 3/01* | (2006.01) |
| *B25J 13/08* | (2006.01) |
| *B25J 9/16* | (2006.01) |

(52) U.S. Cl.
CPC ............ *G06F 3/017* (2013.01); *B25J 9/1612* (2013.01); *B25J 9/1633* (2013.01); *B25J 13/08* (2013.01)

(58) Field of Classification Search
CPC combination set(s) only.
See application file for complete search history.

(56) References Cited

U.S. PATENT DOCUMENTS

| | | | |
|---|---|---|---|
| 6,385,508 B1 * | 5/2002 | McGee | B25J 9/0081 |
| | | | 285/189 |
| 7,936,374 B2 | 5/2011 | Cutler | |
| 9,052,710 B1 * | 6/2015 | Farwell | G05B 19/423 |
| 2003/0093805 A1 | 5/2003 | Gin | |
| 2004/0046736 A1 * | 3/2004 | Pryor | A63F 13/02 |
| | | | 345/156 |
| 2004/0193321 A1 * | 9/2004 | Anfindsen | B25J 9/1664 |
| | | | 700/257 |
| 2005/0075575 A1 | 4/2005 | Vo-Dinh | |

(Continued)

FOREIGN PATENT DOCUMENTS

| | | | | |
|---|---|---|---|---|
| IN | 201641000559 A | * | 1/2016 | ............... G06F 3/00 |
| JP | 2002512069 A | | 4/2002 | |
| KR | 20090006825 A | | 1/2009 | |

OTHER PUBLICATIONS

Skandan, S., "Gesture Controlled Robotic Arm (using Leap Motion)—Components," YouTube, Science & Technology, Copyright May 21, 2014, 2 pages, Retrieved online: <https://www.youtube.com/watch?v=kUqru2KU-xE>.

(Continued)

*Primary Examiner* — Temesghen Ghebretinsae
*Assistant Examiner* — Sosina Abebe
(74) *Attorney, Agent, or Firm* — Haynes Beffel & Wolfeld, LLP; Ernest J. Beffel, Jr.; Paul A. Durdik

(57) ABSTRACT

The technology disclosed relates to motion capture and gesture recognition. In particular, it calculates the exerted force implied by a human hand motion and applies the equivalent through a robotic arm to a target object. In one implementation, this is achieved by tracking the motion and contact of the human hand and generating corresponding robotic commands that replicate the motion and contact of the human hand on a workpiece through a robotic tool.

22 Claims, 20 Drawing Sheets

(56) References Cited

U.S. PATENT DOCUMENTS

| | | | |
|---|---|---|---|
| 2005/0256611 A1* | 11/2005 | Pretlove | B25J 9/1664 700/264 |
| 2005/0279172 A1 | 12/2005 | Schreier et al. | |
| 2008/0036456 A1* | 2/2008 | Kishida | G01R 33/04 324/244 |
| 2008/0198039 A1 | 8/2008 | Philiben | |
| 2009/0076657 A1* | 3/2009 | Tsuboi | G05B 13/021 700/275 |
| 2009/0125146 A1* | 5/2009 | Zhang | B25J 9/1664 700/253 |
| 2009/0231278 A1* | 9/2009 | St. Hilaire | G06F 3/017 345/158 |
| 2011/0107216 A1* | 5/2011 | Bi | G06F 3/011 715/716 |
| 2011/0166709 A1* | 7/2011 | Kim | B25J 9/1612 700/260 |
| 2012/0071891 A1* | 3/2012 | Itkowitz | A61B 19/2203 606/130 |
| 2012/0071892 A1* | 3/2012 | Itkowitz | A61B 19/2203 606/130 |
| 2012/0075428 A1 | 3/2012 | Seki | |
| 2013/0016097 A1 | 1/2013 | Coene et al. | |
| 2013/0182079 A1* | 7/2013 | Holz | G06T 7/593 348/47 |
| 2013/0235163 A1 | 9/2013 | Joo | |
| 2014/0021356 A1 | 1/2014 | Zwaans et al. | |
| 2014/0232631 A1* | 8/2014 | Fleischmann | G06F 3/017 345/156 |
| 2014/0277742 A1* | 9/2014 | Wells | B25J 9/1612 700/264 |
| 2015/0029093 A1* | 1/2015 | Feinstein | G06F 3/03 345/156 |
| 2015/0081098 A1* | 3/2015 | Kogan | B25J 9/1656 700/258 |
| 2015/0290796 A1* | 10/2015 | Iwatake | B25J 9/0081 700/258 |
| 2016/0224202 A1* | 8/2016 | Moskalev | G06Q 10/00 |
| 2016/0229052 A1* | 8/2016 | Touma | B25J 13/06 |
| 2018/0016052 A1* | 1/2018 | Tomioka | B65D 3/22 |

OTHER PUBLICATIONS

Ali, M., "Robotic Arm Gestures Controlled," YouTube, Science and Technology, Copyright Oct. 24, 2013, 4 pages, Retrieved online: <https://www.youtube.com/watch?v=gjGUj5i-yhg>.

Truetechwebs, "Fluid Motion Control Robotic Arm with Your Hand Gestures," YouTube, Entertainment, Copyright Aug. 6, 2013, Retrieved online: <https://www.youtube.com/watch?v=mF_eqfWl7wg>.

Jiang, Y., "How to Build a Robotic Arm That Tracks Your Hand Movements (Part 1)," Jul. 22, 2013, 13 pages, Retrieved online: <http://yujiangtham.com/2013/07/22/how-to-build-a-robotic-arm-that-tracks-your-hand-movements/>.

Hoshino, K., et al., "Copycat Hand for All," University of Tsukuba, AAAI2009: AI Video Competition, Copyright Jun. 20, 2009, 3 pages, Retrieved online: <http://videolectures.net/ijcai09_tomida_cha/>.

Kuchenbecker, K., "Haptography: Digitizing Our Sense of Touch," TED-Ed, YouTube, Copyright Mar. 25, 2013, 3 pages, <https://youtube.com/watch?v=6wJ9Aakddng>.

PCT/US2015/012441—International Search Report and Written Opinion, dated Apr. 9, 2015, 10 pages.

Mann, S., et al., "Video Orbits: Characterizing the Coordinate Transformation Between Two Images Using the Projective Group," MIT Media Lab, Cambridge, Massachusettes, Copyright Feb. 1995, 14 pages.

PCT/US2014/030013—International Search Report, dated Aug. 5, 2014, published as WO 2014-145279, 10 pages.

* cited by examiner

SYSTEMS AND METHODS OF INTERACTING WITH A ROBOTIC TOOL USING FREE-FORM GESTURES

PRIORITY DATA

The application claims the benefit of U.S. Provisional Patent Application No. 62/040,169, entitled, "SYSTEMS AND METHODS OF INTERACTING WITH A ROBOTIC TOOL USING FREE-FORM GESTURES," filed on Aug. 21, 2014. The provisional application is hereby incorporated by reference for all purposes.

FIELD OF THE TECHNOLOGY DISCLOSED

The technology disclosed relates generally to gesture responsive robotics and in particular to real-time generation of robotic commands that emulate and replicate free-form human gestures.

INCORPORATIONS

Materials incorporated by reference in this filing include the following:

"NON-LINEAR MOTION CAPTURE USING FRENET-SERRET FRAMES", U.S. Non-Prov. application Ser. No. 14/338,136, filed 22 Jul. 2014, "DETERMINING POSITIONAL INFORMATION FOR AN OBJECT IN SPACE", U.S. Non-Prov. application Ser. No. 14/214,605, filed 14 Mar. 2014, "RESOURCE-RESPONSIVE MOTION CAPTURE", U.S. Non-Prov. application Ser. No. 14/214,569, filed 14 Mar. 2014, "PREDICTIVE INFORMATION FOR FREE SPACE GESTURE CONTROL AND COMMUNICATION", U.S. Prov. App. No. 61/873,758, filed 4 Sep. 2013, "VELOCITY FIELD INTERACTION FOR FREE SPACE GESTURE INTERFACE AND CONTROL", U.S. Prov. App. No. 61/891,880, filed 16 Oct. 2013, "INTERACTIVE TRAINING RECOGNITION OF FREE SPACE GESTURES FOR INTERFACE AND CONTROL", U.S. Prov. App. No. 61/872,538, filed 30 Aug. 2013, "DRIFT CANCELLATION FOR PORTABLE OBJECT DETECTION AND TRACKING", U.S. Prov. App. No. 61/938,635, filed 11 Feb. 2014, "IMPROVED SAFETY FOR WEARABLE VIRTUAL REALITY DEVICES VIA OBJECT DETECTION AND TRACKING", U.S. Prov. App. No. 61/981,162, filed 17 Apr. 2014, "WEARABLE AUGMENTED REALITY DEVICES WITH OBJECT DETECTION AND TRACKING", U.S. Prov. App. No. 62/001,044, filed 20 May 2014, "METHODS AND SYSTEMS FOR IDENTIFYING POSITION AND SHAPE OF OBJECTS IN THREE-DIMENSIONAL SPACE", US Prov. App. No. 61/587,554, filed 17 Jan. 2012, "SYSTEMS AND METHODS FOR CAPTURING MOTION IN THREE-DIMENSIONAL SPACE", US Prov. App. No. 61/724,091, filed 8 Nov. 2012, "NON-TACTILE INTERFACE SYSTEMS AND METHODS", U.S. Prov. App. No. 61/816,487, filed 26 Apr. 2013, "DYNAMIC USER INTERACTIONS FOR DISPLAY CONTROL", US Prov. App. No. 61/752,725, filed 15 Jan. 2013, "VEHICLE MOTION SENSORY CONTROL", U.S. Prov. App. No. 62/005,981, filed 30 May 2014, "NON-LINEAR MOTION CAPTURE USING FRENET-SERRET FRAMES", U.S. Non-Prov. application Ser. No. 14/338,136, filed 22 Jul. 2014, "MOTION CAPTURE USING CROSS-SECTIONS OF AN OBJECT", U.S. application Ser. No. 13/414,485, filed 7 Mar. 2012, and "SYSTEM AND METHODS FOR CAPTURING MOTION IN THREE-DIMENSIONAL SPACE", U.S. application Ser. No. 13/742,953, filed 16 Jan. 2013.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves may also correspond to implementations of the claimed technology.

The technology disclosed relates to motion capture and gesture recognition. In particular, it calculates the exerted force implied by a human hand motion and applies the equivalent through a robotic arm to a target object. In one implementation, this is achieved by tracking the motion and contact of the human hand and generating corresponding robotic commands that replicate the motion and contact of the human hand on a workpiece through a robotic tool.

The human hand is complex entity capable of both gross grasp and fine motor skills. Despite many successful high-level skeletal control techniques, modelling realistic hand motion remains tedious and challenging. It has been a formidable challenge to emulate and articulate the complex and expressive form, function, and communication of the human hand.

In addition, robotics is evolving rapidly, and its applications in the industry is also increasing from object pick and place robots, to move and locate robots. In fact, the field of robotics is moving so quickly, that the field encompasses a wider range of disciplines and applications than taught by traditional robotics education; which must adapt and incorporate a more multidisciplinary approach. One discipline that needs greater inclusion in robotics includes improved robot communication and interaction.

Existing gesture recognition techniques utilize conventional motion capture approaches that rely on markers or sensors worn by the occupant while executing activities and/or on the strategic placement of numerous bulky and/or complex equipment in specialized smart home environments to capture occupant movements. Unfortunately, such systems tend to be expensive to construct. In addition, markers or sensors worn by the occupant can be cumbersome and interfere with the occupant's natural movement. Further, systems involving large numbers of cameras tend not to operate in real time, due to the volume of data that needs to be analyzed and correlated. Such considerations have limited the deployment and use of motion capture technology.

Consequently, there is a need for improved techniques to capture the motion of objects in real time without attaching sensors or markers thereto and to facilitate recognition of dynamic gestures for robotics applications.

SUMMARY

A simplified summary is provided herein to help enable a basic or general understanding of various aspects of exemplary, non-limiting implementations that follow in the more detailed description and the accompanying drawings. This summary is not intended, however, as an extensive or exhaustive overview. Instead, the sole purpose of this summary is to present some concepts related to some exemplary non-limiting implementations in a simplified form as a prelude to the more detailed description of the various implementations that follow.

The technology disclosed relates to motion capture and gesture recognition for robotics applications. In particular, an exerted force implied by a human hand motion can be determined and an equivalent can be applied through a robotic arm to a target object. In one implementation, this is achieved by tracking the motion and contact of the human hand and generating corresponding robotic commands that replicate the motion and contact of the human hand on a workpiece through a robotic tool.

Other aspects and advantages of the technology disclosed can be seen on review of the drawings, the detailed description and the claims, which follow.

BRIEF DESCRIPTION OF THE DRAWINGS

In the drawings, like reference characters generally refer to like parts throughout the different views. Also, the drawings are not necessarily to scale, with an emphasis instead generally being placed upon illustrating the principles of the technology disclosed. In the following description, various implementations of the technology disclosed are described with reference to the following drawings, in which:

FIG. 6B shows one implementation of gestural data of one or more free-form gestures performed using a hand.

DETAILED DESCRIPTION

Introduction

Figure 1:
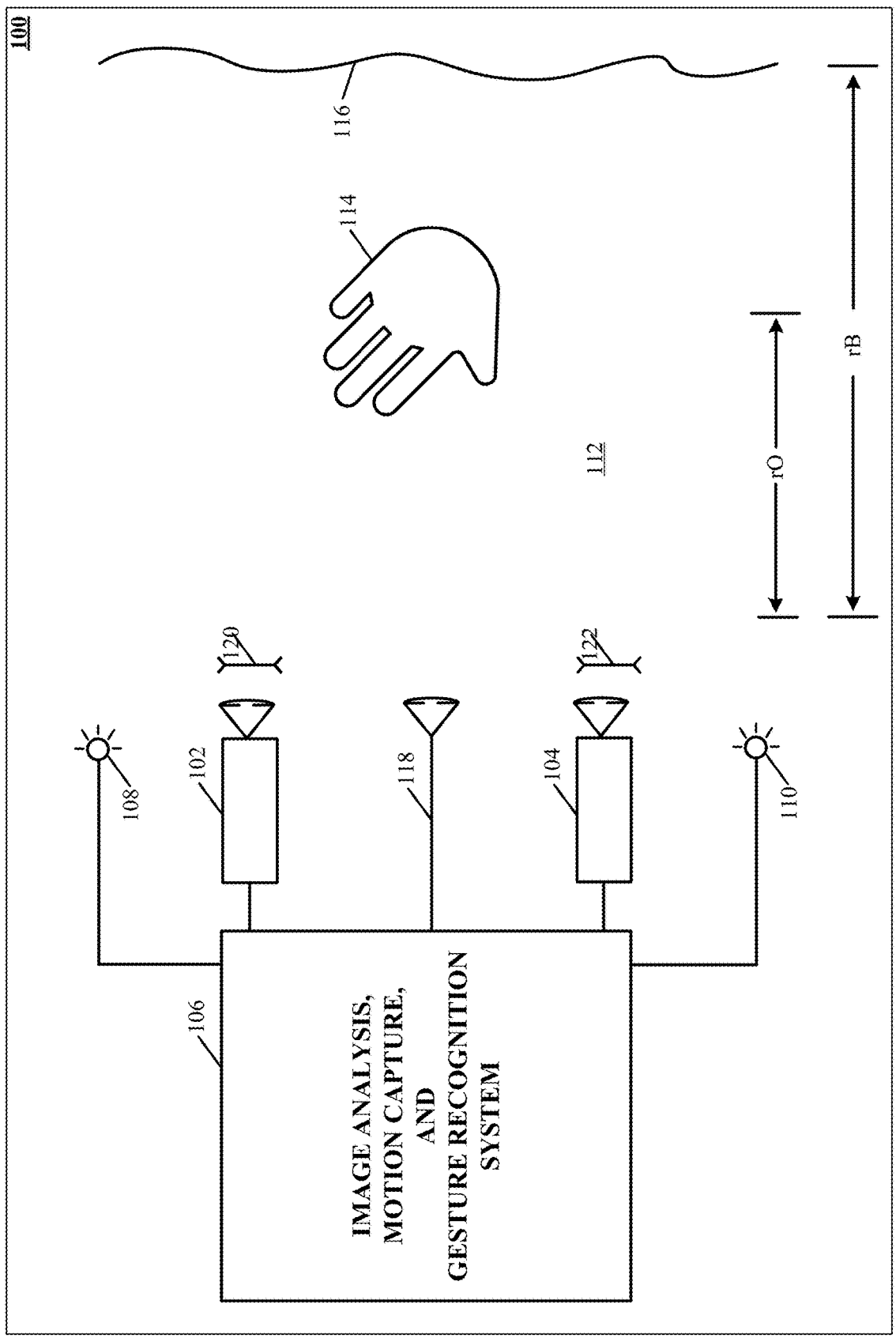
FIG. 1 illustrates an example gesture-recognition system.

The technology disclosed presents a gesture based human-robot interface that enables users to manipulate a robotic arm by demonstrating free-form gestures. The technology disclosed can provide synchronized robotic arm control that emulates and replicates human free-form gestures. Some implementations can provide advantages such as intuitive tools for robotic manipulation that empower non-experts to interact with robots. The technology disclosed can be applied to a plurality of disciplines including development of prosthetic hands, robotic modelling and planning, biomechanics, defense, or architecture and design.

Traditionally and currently robots are controlled by pre-loaded codes or legacy input devices such as joysticks, keyboards, mice, etc. Legacy input devices such as joysticks, keyboards, or mice are not suitable to control the modern robotic devices with high degrees of freedom and precise end-effectors. Using keyboards or keypads to control the motion of a robotic arm in a three-dimensional space is very cumbersome and highly error-prone.

In general, existing motion sensors are more intrusive, expensive, have cable connections, are not portable, and require expertise to set up. Also, existing motion sensor designs perform incomplete tracking with performance ratings only good in theory and fail to capture the subtleties of hand motion.

The appearance-based or shape detection considers only a handful of gestures that are quite different among them, fitting the actual gesture to the closest in the database and identifying the hand posture by searching a similar image from a vast database, optimized for quick searching. Much of the work in this area treats the hand as a volumetric solid that can grasp and manipulate objects, but generally does not deal with the fine motor capabilities of the fingers.

Further, traditional construction of 3D models of a hand for gathering positional information includes joints that have pre-assigned location and direction. This pre-assignment hampers the fitting to the real motion data. Moreover, conventional 3D models are unrealistically defined, having much more or much less freedom than real human hand joints do. In addition, most of these gesture recognition systems require a first pre-defined pose in order to better identify and tracks object. However, such work does not capture the interdependencies that exist among the joints of different fingers.

The technology disclosed allows for advance control of a robotic arm that emulates and replicates user gesture control such as spread of the palm, clenching of the fist, and the curling of each finger. The technology disclosed generates a 3D solid model that includes joints with locations and orientations, which can accurately capture actual geometry of the human hand during a free-form gesture such as edge information of fingers and palms including points within and/or periphery of the fingers and palms, resulting in a much more accurate model and motion angles, according to one implementation. In another implementation, the technology disclosed can be adapted to capture the motion of any other body part such as a head, legs, or torso. The technology disclosed also allows for dexterous manipulation and grasping of a work piece through a robotic tool that is responsive to free-form hand gestures. Dexterous manipulation allows for changing the position and orientation of the workpiece. Grasping relates to controlling the force applied to the workpiece.

The technology disclosed allows for advance control of a robotic arm that emulates and replicates user gesture control. Examples of systems, apparatus, and methods according to the disclosed implementations are described in a "robotic arm" context. The examples of "robotic arm" are being provided solely to add context and aid in the understanding of the disclosed implementations. In other instances, examples of gesture-based robotic interactions in other contexts like virtual tools, surgical tools, industrial machinery, gaming devices, etc. may be used. Other applications are possible, such that the following examples should not be taken as definitive or limiting either in scope, context, or setting. It will thus be apparent to one skilled in the art that implementations may be practiced in or outside the "robotic arm" context.

As used herein, a given signal, event or value is "responsive to" a predecessor signal, event or value of the predecessor signal, event or value influenced by the given signal, event or value. If there is an intervening processing element, step or time period, the given signal, event or value can still be "responsive to" the predecessor signal, event or value. If the intervening processing element or step combines more than one signal, event or value, the signal output of the processing element or step is considered "responsive to" each of the signal, event or value inputs. If the given signal, event or value is the same as the predecessor signal, event or value, this is merely a degenerate case in which the given signal, event or value is still considered to be "responsive to" the predecessor signal, event or value. "Responsiveness" or "dependency" or "basis" of a given signal, event or value upon another signal, event or value is defined similarly.

As used herein, the "identification" of an item of information does not necessarily require the direct specification of that item of information. Information can be "identified" in a field by simply referring to the actual information through one or more layers of indirection, or by identifying one or more items of different information which are together sufficient to determine the actual item of information. In addition, the term "specify" is used herein to mean the same as "identify."

Gesture Recognition System

The term "motion capture" refers generally to processes that capture movement of a subject in three dimensional (3D) space and translate that movement into, for example, a digital model or other representation. Motion capture is typically used with complex subjects that have multiple separately articulating members whose spatial relationships change as the subject moves. For instance, if the subject is a walking person, not only does the whole body move across space, but the positions of arms and legs relative to the person's core or trunk are constantly shifting. Motion-capture systems are typically designed to model this articulation.

Motion capture systems can utilize one or more cameras to capture sequential images of an object in motion, and computers to analyze the images to create a reconstruction of an object's shape, position, and orientation as a function of time. For 3D motion capture, at least two cameras are typically used. Image-based motion-capture systems rely on the ability to distinguish an object of interest from a background. This is often achieved using image-analysis algorithms that detect edges, typically by comparing pixels to detect abrupt changes in color and/or brightness. Conventional systems, however, suffer performance degradation under many common circumstances, e.g., low contrast between the object of interest and the background and/or patterns in the background that may falsely register as object edges.

Referring first to FIG. 1, which illustrates an exemplary motion-capture system 100 including any number of cameras 102, 104 coupled to an image analysis, motion capture, and gesture recognition system 106 (The system 106 is hereinafter variably referred to as the "image analysis and motion capture system," the "gesture recognition system," the "image analysis system," the "motion capture system," the "control system," the "control and image-processing system," the "control system," or the "image-processing system," depending on which functionality of a specific system implementation is being discussed). Cameras 102, 104 provide digital image data to the image analysis, motion capture, and gesture recognition system 106, which analyzes the image data to determine the three-dimensional (3D) position, orientation, and/or motion of the object 114 the field of view of the cameras 102, 104. Cameras 102, 104 can be any type of cameras, including cameras sensitive across the visible spectrum (e.g., red-green-blue or RGB) or, more typically, with enhanced sensitivity to a confined wavelength band (e.g., the infrared (IR) or ultraviolet (UV) bands)) or combinations thereof; more generally, the term "camera" herein refers to any device (or combination of devices) capable of capturing an image of an object and representing that image in the form of digital data. Information received from pixels of cameras 102, 104 sensitive to IR light can be separated from information received from pixels sensitive to visible light, e.g., RGB (red, green, and blue) and these two types of image information can be processed separately. For example, information from one type of light can be used to correct or corroborate information determined from a second type of light. In another example, information from different types of light can be used for different purposes.

While illustrated using an example of a two camera implementation, other implementations are readily achievable using different numbers of cameras or non-camera light sensitive image sensors or combinations thereof. For example, line sensors or line cameras rather than conventional devices that capture a two-dimensional (2D) image can be employed. Further, the term "light" is used generally to connote any electromagnetic radiation, which may or may not be within the visible spectrum, and can be broadband (e.g., white light) or narrowband (e.g., a single wavelength or narrow band of wavelengths).

Cameras 102, 104 are preferably capable of capturing video images (i.e., successive image frames at a constant rate of at least 15 frames per second); although no particular frame rate is required. The capabilities of cameras 102, 104 are not critical to the technology disclosed, and the cameras can vary as to frame rate, image resolution (e.g., pixels per image), color or intensity resolution (e.g., number of bits of intensity data per pixel), focal length of lenses, depth of field, etc. In general, for a particular application, any cameras capable of focusing on objects within a spatial volume of interest can be used. For instance, to capture motion of the hand of an otherwise stationary person, the volume of interest can be defined as a cube approximately one meter on a side. To capture motion of a running person, the volume of interest might have dimensions of tens of meters in order to observe several strides.

Cameras 102, 104 can be oriented in any convenient manner. In one implementation, the optical axes of the cameras 102, 104 are parallel, but this is not required. As described below, one or more of the cameras 102, 104 can be used to define a "vantage point" from which the object 114 is seen; if the location and view direction associated with each vantage point are known, the locus of points in space that project onto a particular position in the cameras' image plane can be determined. In some implementations, motion capture is reliable only for objects in an area where the fields of view of cameras 102, 104; the cameras 102, 104 can be arranged to provide overlapping fields of view throughout the area where motion of interest is expected to occur.

In some implementations, the illustrated system 100 includes one or more sources 108, 110, which can be disposed to either side of cameras 102, 104, and are controlled by gesture recognition system 106. In one implementation, the sources 108, 110 are light sources. For example, the light sources can be infrared light sources, e.g., infrared light emitting diodes (LEDs), and cameras 102, 104 can be sensitive to infrared light. Use of infrared light can allow the motion-capture system 100 to operate under a broad range of lighting conditions and can avoid various inconveniences or distractions that can be associated with directing visible light into the region where the person is moving. However, a particular wavelength or region of the electromagnetic spectrum can be required. In one implementation, filters 120, 122 are placed in front of cameras 102, 104 to filter out visible light so that only infrared light is registered in the images captured by cameras 102, 104.

In another implementation, the sources 108, 110 are sonic sources providing sonic energy appropriate to one or more sonic sensors (not shown in FIG. 1 for clarity sake) used in conjunction with, or instead of, cameras 102, 104. The sonic sources transmit sound waves to the user; with the user either blocking ("sonic shadowing") or altering the sound waves ("sonic deflections") that impinge upon her. Such sonic shadows and/or deflections can also be used to detect the user's gestures and/or provide presence information and/or distance information using ranging techniques. In some implementations, the sound waves are, for example, ultrasound, which are not audible to humans.

It should be stressed that the arrangement shown in FIG. 1 is representative and not limiting. For example, lasers or other light sources can be used instead of LEDs. In implementations that include laser(s), additional optics (e.g., a lens or diffuser) can be employed to widen the laser beam (and make its field of view similar to that of the cameras). Useful arrangements can also include short-angle and wide-angle illuminators for different ranges. Light sources are typically diffuse rather than specular point sources; for example, packaged LEDs with light-spreading encapsulation are suitable.

In operation, light sources 108, 110 are arranged to illuminate a region of interest 112 that includes an entire control object or its portion 114 (in this example, a hand) that can optionally hold a tool or other object of interest. Cameras 102, 104 are oriented toward the region 112 to capture video images of the hand 114. In some implementations, the operation of light sources 108, 110 and cameras 102, 104 is controlled by the gesture recognition system 106, which can be, e.g., a computer system, control logic implemented in hardware and/or software or combinations thereof. Based on the captured images, gesture recognition system 106 determines the position and/or motion of hand 114.

Motion capture can be improved by enhancing contrast between the object of interest 114 and background surfaces like surface 116 visible in an image, for example, by means of controlled lighting directed at the object. For instance, in motion capture system 106 where an object of interest 114, such as a person's hand, is significantly closer to the cameras 102 and 104 than the background surface 116, the falloff of light intensity with distance ($1/r^2$ for point like light sources) can be exploited by positioning a light source (or multiple light sources) near the camera(s) or other image-capture device(s) and shining that light onto the object 114. Source light reflected by the nearby object of interest 114 can be expected to be much brighter than light reflected from more distant background surface 116, and the more distant the background (relative to the object), the more pronounced the effect will be. Accordingly, a threshold cut off on pixel brightness in the captured images can be used to distinguish "object" pixels from "background" pixels. While broadband ambient light sources can be employed, various implementations use light having a confined wavelength range and a camera matched to detect such light; for example, an infrared source light can be used with one or more cameras sensitive to infrared frequencies.

In operation, cameras 102, 104 are oriented toward a region of interest 112 in which an object of interest 114 (in this example, a hand) and one or more background objects 116 can be present. Light sources 108, 110 are arranged to illuminate region 112. In some implementations, one or more of the light sources 108, 110 and one or more of the cameras 102, 104 are disposed opposite the motion to be detected, e.g., in the case of hand motion, on a table or other surface beneath the spatial region where hand motion occurs. In this location, the amount of information recorded about the hand is proportional to the number of pixels it occupies in the camera images, and the hand will occupy more pixels when the camera's angle with respect to the hand's "pointing direction" is as close to perpendicular as possible. Further, if the cameras 102, 104 are looking up, there is little likelihood of confusion with background objects (clutter on the user's desk, for example) and other people within the cameras' field of view. In an alternative implementation, the cameras 102, 104 are disposed along the motion detected, e.g., where the object 114 is expected to move.

Control and image-processing system 106, which can be, e.g., a computer system, can control the operation of light sources 108, 110 and cameras 102, 104 to capture images of region 112. Based on the captured images, the image-processing system 106 determines the position and/or motion of object 114. For example, as a step in determining the position of object 114, image-analysis system 106 can determine which pixels of various images captured by cameras 102, 104 contain portions of object 114. In some implementations, any pixel in an image can be classified as an "object" pixel or a "background" pixel depending on whether that pixel contains a portion of object 114 or not.

With the use of light sources 108, 110, classification of pixels as object or background pixels can be based on the brightness of the pixel. For example, the distance ($r_O$) between an object of interest 114 and cameras 102, 104 is expected to be smaller than the distance ($r_B$) between background object(s) 116 and cameras 102, 104. Because the intensity of light from sources 108, 110 decreases as $1/r^2$, object 114 will be more brightly lit than background 116, and pixels containing portions of object 114 (i.e., object pixels) will be correspondingly brighter than pixels containing portions of background 116 (i.e., background pixels).

For example, if $r_B/r_O=2$, then object pixels will be approximately four times brighter than background pixels, assuming object 114 and background 116 are similarly reflective of the light from sources 108, 110, and further assuming that the overall illumination of region 112 (at least within the frequency band captured by cameras 102, 104) is dominated by light sources 108, 110. These conditions generally hold for suitable choices of cameras 102, 104, light sources 108, 110, filters 120, 122, and objects commonly encountered. For example, light sources 108, 110 can be infrared LEDs capable of strongly emitting radiation in a narrow frequency band, and filters 120, 122 can be matched to the frequency band of light sources 108, 110. Thus, although a human hand or body, or a heat source or other object in the background, can emit some infrared radiation, the response of cameras 102, 104 can still be dominated by light originating from sources 108, 110 and reflected by object 114 and/or background 116.

In this arrangement, image-analysis system 106 can quickly and accurately distinguish object pixels from background pixels by applying a brightness threshold to each pixel. For example, pixel brightness in a CMOS sensor or similar device can be measured on a scale from 0.0 (dark) to 1.0 (fully saturated), with some number of gradations in between depending on the sensor design. The brightness encoded by the camera pixels scales standardly (linearly) with the luminance of the object, typically due to the deposited charge or diode voltages. In some implementations, light sources 108, 110 are bright enough that reflected light from an object at distance $r_O$ produces a brightness level of 1.0 while an object at distance $n3=2r_O$ produces a brightness level of 0.25. Object pixels can thus be readily distinguished from background pixels based on brightness. Further, edges of the object can also be readily detected based on differences in brightness between adjacent pixels, allowing the position of the object within each image to be determined. Correlating object positions between images from cameras 102, 104 allows image-analysis system 106 to determine the location in 3D space of object 114, and analyzing sequences of images allows image-analysis system 106 to reconstruct 3D motion of object 114 using motion algorithms.

In accordance with various implementations of the technology disclosed, the cameras 102, 104 (and typically also the associated image-analysis functionality of gesture recognition system 106) are operated in a low-power mode until an object of interest 114 is detected in the region of interest 112. For purposes of detecting the entrance of an object of interest 114 into this region, the system 100 further includes one or more light sensors 118 (e.g., a CCD or CMOS sensor) and/or an associated imaging optic (e.g., a lens) that monitor the brightness in the region of interest 112 and detect any change in brightness. For example, a single light sensor including, e.g., a photodiode that provides an output voltage indicative of (and over a large range proportional to) a measured light intensity can be disposed between the two cameras 102, 104 and oriented toward the region of interest 112. The one or more sensors 118 continuously measure one or more environmental illumination parameters such as the brightness of light received from the environment. Under static conditions—which implies the absence of any motion in the region of interest 112—the brightness will be constant. If an object enters the region of interest 112, however, the brightness can abruptly change. For example, a person walking in front of the sensor(s) 118 can block light coming from an opposing end of the room, resulting in a sudden decrease in brightness. In other situations, the person can reflect light from a light source in the room onto the sensor, resulting in a sudden increase in measured brightness.

The aperture of the sensor(s) 118 can be sized such that its (or their collective) field of view overlaps with that of the cameras 102, 104. In some implementations, the field of view of the sensor(s) 118 is substantially co-existent with that of the cameras 102, 104 such that substantially all objects entering the camera field of view are detected. In other implementations, the sensor field of view encompasses and exceeds that of the cameras. This enables the sensor(s) 118 to provide an early warning if an object of interest approaches the camera field of view. In yet other implementations, the sensor(s) capture(s) light from only a portion of the camera field of view, such as a smaller area of interest located in the center of the camera field of view.

Gesture recognition system 106 monitors the output of the sensor(s) 118, and if the measured brightness changes by a set amount (e.g., by 10% or a certain number of candela), it recognizes the presence of an object of interest in the region of interest 112. The threshold change can be set based on the geometric configuration of the region of interest and the motion-capture system, the general lighting conditions in the area, the sensor noise level, and the expected size, proximity, and reflectivity of the object of interest so as to minimize both false positives and false negatives. In some implementations, suitable settings are determined empirically, e.g., by having a person repeatedly walk into and out of the region of interest 112 and tracking the sensor output to establish a minimum change in brightness associated with the person's entrance into and exit from the region of interest 112. Of course, theoretical and empirical threshold-setting methods can also be used in conjunction. For example, a range of thresholds can be determined based on theoretical considerations (e.g., by physical modelling, which can include ray tracing, noise estimation, etc.), and the threshold thereafter fine-tuned within that range based on experimental observations.

In implementations where the area of interest 112 is illuminated, the sensor(s) 118 will generally, in the absence of an object in this area, only measure scattered light amounting to a small fraction of the illumination light. Once an object enters the illuminated area, however, this object can reflect substantial portions of the light toward the sensor(s) 118, causing an increase in the measured brightness. In some implementations, the sensor(s) 118 is (or are) used in conjunction with the light sources 108, 110 to deliberately measure changes in one or more environmental illumination parameters such as the reflectivity of the environment within the wavelength range of the light sources. The light sources can "blink" e.g., change activation states, and a brightness differential be measured between dark and light periods of the blinking cycle. If no object is present in the illuminated region, this yields a baseline reflectivity of the environment. Once an object is in the area of interest 112, the brightness differential will increase substantially, indicating increased reflectivity. (Typically, the signal measured during dark periods of the blinking cycle, if any, will be largely unaffected, whereas the reflection signal measured during the light period will experience a significant boost.)

Accordingly, the control system 106 monitoring the output of the sensor(s) 118 can detect an object in the region of interest 112 based on a change in one or more environmental illumination parameters such as environmental reflectivity that exceeds a predetermined threshold (e.g., by 10% or some other relative or absolute amount). As with changes in brightness, the threshold change can be set theoretically based on the configuration of the image-capture system and the monitored space as well as the expected objects of interest, and/or experimentally based on observed changes in reflectivity.

Computer System

Figure 2:
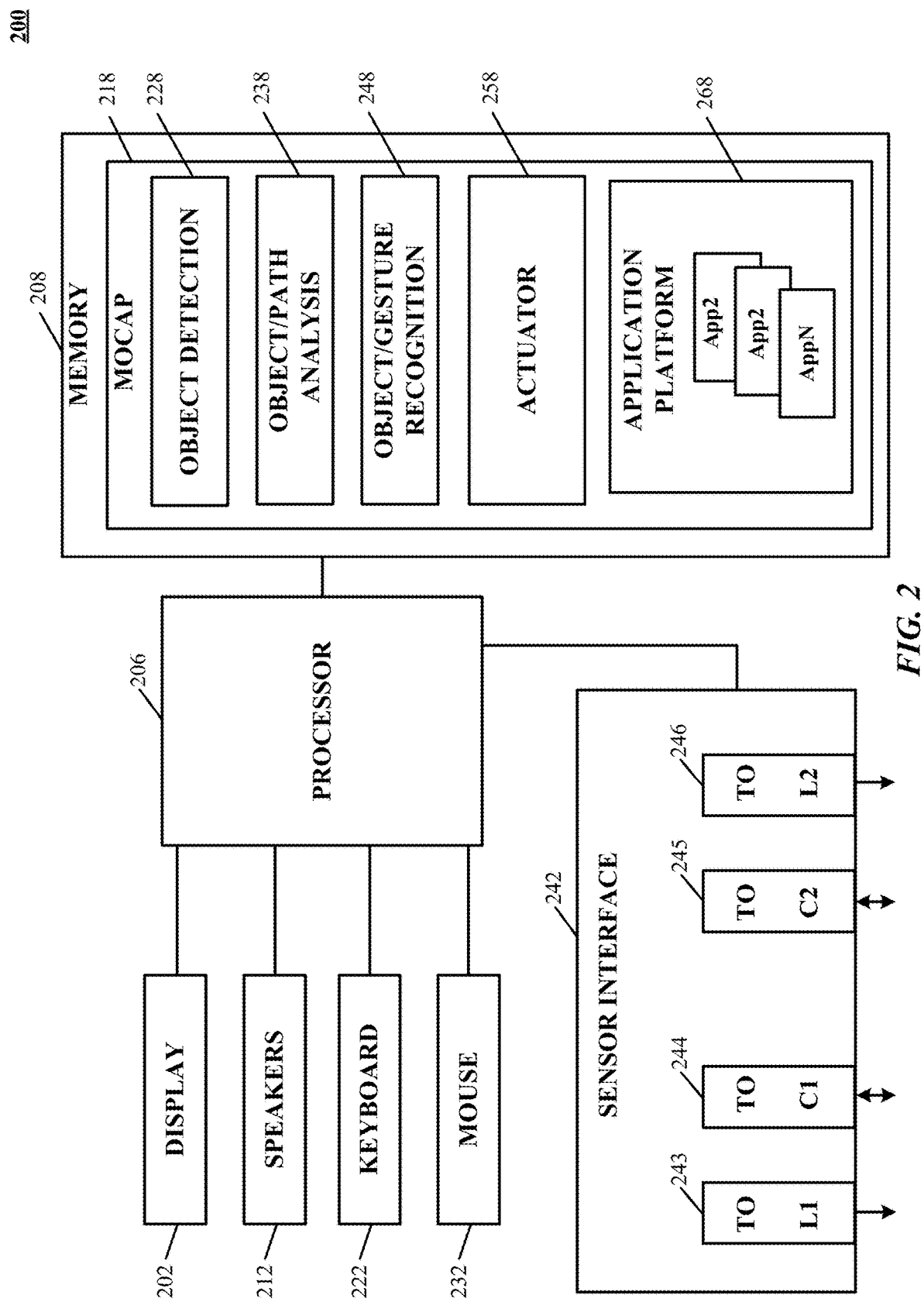
FIG. 2 is a simplified block diagram of a computer system implementing a gesture-recognition apparatus according to an implementation of the technology disclosed.

FIG. 2 is a simplified block diagram of a computer system 200, implementing gesture recognition system 106 according to an implementation of the technology disclosed. Gesture recognition system 106 can include or consist of any device or device component that is capable of capturing and processing image data. In some implementations, computer system 200 includes a processor 206, memory 208, a sensor interface 242, a display 202 (or other presentation mechanism(s), e.g. holographic projection systems, wearable googles or other head mounted displays (HMDs), heads up displays (HUDs), other visual presentation mechanisms or combinations thereof, speakers 212, a keyboard 222, and a mouse 232. Memory 208 can be used to store instructions to be executed by processor 206 as well as input and/or output data associated with execution of the instructions. In particular, memory 208 contains instructions, conceptually illustrated as a group of modules described in greater detail below, that control the operation of processor 206 and its interaction with the other hardware components.

An operating system directs the execution of low-level, basic system functions such as memory allocation, file management and operation of mass storage devices. The operating system may be or include a variety of operating systems such as Microsoft WINDOWS operating system, the Unix operating system, the Linux operating system, the Xenix operating system, the IBM AIX operating system, the Hewlett Packard UX operating system, the Novell NETWARE operating system, the Sun Microsystems SOLARIS operating system, the OS/2 operating system, the BeOS operating system, the MAC OS operating system, the APACHE operating system, an OPENACTION operating system, iOS, Android or other mobile operating systems, or another operating system platform.

The computing environment can also include other removable/non-removable, volatile/nonvolatile computer storage media. For example, a hard disk drive can read or write to non-removable, nonvolatile magnetic media. A magnetic disk drive can read from or write to a removable, nonvolatile magnetic disk, and an optical disk drive can read from or write to a removable, nonvolatile optical disk such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid physical arrangement RAM, solid physical arrangement ROM, and the like. The storage media are typically connected to the system bus through a removable or non-removable memory interface.

According to some implementations, cameras 102, 104 and/or light sources 108, 110 can connect to the computer 200 via a universal serial bus (USB), FireWire, or other cable, or wirelessly via Bluetooth, Wi-Fi, etc. The computer 200 can include a sensor interface 242, implemented in hardware (e.g., as part of a USB port) and/or software (e.g., executed by processor 206), that enables communication with the cameras 102, 104 and/or light sources 108, 110. The camera interface 242 can include one or more data ports and associated image buffers for receiving the image frames from the cameras 102, 104; hardware and/or software signal processors to modify the image data (e.g., to reduce noise or reformat data) prior to providing it as input to a motion-capture or other image-processing program; and/or control signal ports for transmit signals to the cameras 102, 104, e.g., to activate or deactivate the cameras, to control camera settings (frame rate, image quality, sensitivity, etc.), or the like.

Processor 206 can be a general-purpose microprocessor, but depending on implementation can alternatively be a microcontroller, peripheral integrated circuit element, a CSIC (customer-specific integrated circuit), an ASIC (application-specific integrated circuit), a logic circuit, a digital signal processor, a programmable logic device such as an FPGA (field-programmable gate array), a PLD (programmable logic device), a PLA (programmable logic array), an RFID processor, smart chip, or any other device or arrangement of devices that is capable of implementing the actions of the processes of the technology disclosed.

Sensor interface 242 can include hardware and/or software that enables communication between computer system 200 and cameras such as cameras 102, 104 shown in FIG. 1, as well as associated light sources such as light sources 108, 110 of FIG. 1. Thus, for example, sensor interface 242 can include one or more data ports 243, 244, 245, 246 to which cameras can be connected, as well as hardware and/or software signal processors to modify data signals received from the cameras (e.g., to reduce noise or reformat data) prior to providing the signals as inputs to a motion-capture ("mocap") program 218 executing on processor 206. In some implementations, sensor interface 242 can also transmit signals to the cameras, e.g., to activate or deactivate the cameras, to control camera settings (frame rate, image quality, sensitivity, etc.), or the like. Such signals can be transmitted, e.g., in response to control signals from processor 206, which can in turn be generated in response to user input or other detected events.

Sensor interface 242 can also include controllers 243, 246, to which light sources (e.g., light sources 108, 110) can be connected. In some implementations, controllers 243, 246 provide operating current to the light sources, e.g., in response to instructions from processor 206 executing mocap program 218. In other implementations, the light sources can draw operating current from an external power supply, and controllers 243, 246 can generate control signals for the light sources, e.g., instructing the light sources to be turned on or off or changing the brightness. In some implementations, a single controller can be used to control multiple light sources.

Instructions defining mocap program 218 are stored in memory 208, and these instructions, when executed, perform motion-capture analysis on images supplied from cameras connected to sensor interface 242. In one implementation, mocap program 218 includes various modules, such as an object detection module 228, an object analysis module 238, and a gesture-recognition module 248. Object detection module 228 can analyze images (e.g., images captured via sensor interface 242) to detect edges of an object therein and/or other information about the object's location. Object analysis module 238 can analyze the object information provided by object detection module 228 to determine the 3D position and/or motion of the object (e.g., a user's hand). Examples of operations that can be implemented in code modules of mocap program 218 are described below. Memory 208 can also include other information and/or code modules used by mocap program 218 such as an application platform 268, which allows a user to interact with the mocap program 218 using different applications like application 1 (App1), application 2 (App2), and application N (AppN).

Display 202, speakers 212, keyboard 222, and mouse 232 can be used to facilitate user interaction with computer system 200. In some implementations, results of gesture capture using sensor interface 242 and mocap program 218 can be interpreted as user input. For example, a user can perform hand gestures that are analyzed using mocap program 218, and the results of this analysis can be interpreted as an instruction to some other program executing on processor 206 (e.g., a web browser, word processor, or other application). Thus, by way of illustration, a user might use upward or downward swiping gestures to "scroll" a webpage currently displayed on display 202, to use rotating gestures to increase or decrease the volume of audio output from speakers 212, and so on.

It will be appreciated that computer system 200 is illustrative and that variations and modifications are possible. Computer systems can be implemented in a variety of form factors, including server systems, desktop systems, laptop systems, tablets, smart phones or personal digital assistants, wearable devices, e.g., goggles, head mounted displays (HMDs), wrist computers, and so on. A particular implementation can include other functionality not described herein, e.g., wired and/or wireless network interfaces, media playing and/or recording capability, etc. In some implementations, one or more cameras can be built into the computer or other device into which the sensor is imbedded rather than being supplied as separate components. Further, an image analyzer can be implemented using only a subset of computer system components (e.g., as a processor executing program code, an ASIC, or a fixed-function digital signal processor, with suitable I/O interfaces to receive image data and output analysis results).

In another example, in some implementations, the cameras 102, 104 are connected to or integrated with a special-purpose processing unit that, in turn, communicates with a general-purpose computer, e.g., via direct memory access ("DMA"). The processing unit can include one or more image buffers for storing the image data read out from the camera sensors, a GPU or other processor and associated memory implementing at least part of the motion-capture algorithm, and a DMA controller. The processing unit can provide processed images or other data derived from the camera images to the computer for further processing. In some implementations, the processing unit sends display control signals generated based on the captured motion (e.g., of a user's hand) to the computer, and the computer uses these control signals to adjust the on-screen display of documents and images that are otherwise unrelated to the camera images (e.g., text documents or maps) by, for example, shifting or rotating the images.

While computer system 200 is described herein with reference to particular blocks, it is to be understood that the blocks are defined for convenience of description and are not intended to imply a particular physical arrangement of component parts. Further, the blocks need not correspond to physically distinct components. To the extent that physically distinct components are used, connections between components (e.g., for data communication) can be wired and/or wireless as desired.

With reference to FIGS. 1 and 2, the user performs a gesture that is captured by the cameras 102, 104 as a series of temporally sequential images. In other implementations, cameras 102, 104 can capture any observable pose or portion of a user. For instance, if a user walks into the field of view near the cameras 102, 104, cameras 102, 104 can capture not only the whole body of the user, but the positions of arms and legs relative to the person's core or trunk. These are analyzed by a gesture-recognition module 248, which can be implemented as another module of the mocap 218. Gesture-recognition module 248 provides input to an electronic device, allowing a user to remotely control the electronic device and/or manipulate virtual objects, such as prototypes/models, blocks, spheres, or other shapes, buttons, levers, or other controls, in a virtual environment displayed on display 202.

The user can perform the gesture using any part of her body, such as a finger, a hand, or an arm. As part of gesture recognition or independently, the gesture recognition system 106 can determine the shapes and positions of the user's hand in 3D space and in real time; see, e.g., U.S. Ser. Nos. 61/587,554, 13/414,485, 61/724,091, and 13/724,357 filed on Jan. 17, 2012, Mar. 7, 2012, Nov. 8, 2012, and Dec. 21, 2012 respectively, the entire disclosures of which are hereby incorporated by reference. As a result, the image analysis and motion capture system processor 206 can not only recognize gestures for purposes of providing input to the electronic device, but can also capture the position and shape of the user's hand in consecutive video images in order to characterize the hand gesture in 3D space and reproduce it on the display screen 202.

In one implementation, the gesture-recognition module 248 compares the detected gesture to a library of gestures electronically stored as records in a database, which is implemented in the gesture-recognition system 106, the electronic device, or on an external storage system. (As used herein, the term "electronically stored" includes storage in volatile or non-volatile storage, the latter including disks, Flash memory, etc., and extends to any computationally addressable storage media (including, for example, optical storage).) For example, gestures can be stored as vectors, i.e., mathematically specified spatial trajectories, and the gesture record can have a field specifying the relevant part of the user's body making the gesture; thus, similar trajectories executed by a user's hand and head can be stored in the database as different gestures so that an application can interpret them differently. Typically, the trajectory of a sensed gesture is mathematically compared against the stored trajectories to find a best match, and the gesture is recognized as corresponding to the located database entry only if the degree of match exceeds a threshold. The vector can be scaled so that, for example, large and small arcs traced by a user's hand will be recognized as the same gesture (i.e., corresponding to the same database record) but the gesture recognition module will return both the identity and a value, reflecting the scaling, for the gesture. The scale can correspond to an actual gesture distance traversed in performance of the gesture, or can be normalized to some canonical distance.

In various implementations, the motion captured in a series of camera images is used to compute a corresponding series of output images for presentation on the display 202. For example, camera images of a moving hand can be translated by the processor 206 into a wire-frame or other graphical representations of motion of the hand. In any case, the output images can be stored in the form of pixel data in a frame buffer, which can, but need not be, implemented, in main memory 208. A video display controller reads out the frame buffer to generate a data stream and associated control signals to output the images to the display 202. The video display controller can be provided along with the processor 206 and memory 208 on-board the motherboard of the computer 200, and can be integrated with the processor 206 or implemented as a co-processor that manipulates a separate video memory.

In some implementations, the computer 200 is equipped with a separate graphics or video card that aids with generating the feed of output images for the display 202. The video card generally includes a graphical processing unit ("GPU") and video memory, and is useful, in particular, for complex and computationally expensive image processing and rendering. The graphics card can implement the frame buffer and the functionality of the video display controller (and the on-board video display controller can be disabled). In general, the image-processing and motion-capture functionality of the system 200 can be distributed between the GPU and the main processor 206.

In some implementations, the gesture-recognition module 248 detects more than one gesture. The user can perform an arm-waving gesture while flexing his or her fingers. The gesture-recognition module 248 detects the waving and flexing gestures and records a waving trajectory and five flexing trajectories for the five fingers. Each trajectory can be converted into a vector along, for example, six Euler degrees of freedom in Euler space. The vector with the largest magnitude can represent the dominant component of the motion (e.g., waving in this case) and the rest of vectors can be ignored. In one implementation, a vector filter that can be implemented using conventional filtering techniques is applied to the multiple vectors to filter the small vectors out and identify the dominant vector. This process can be repetitive, iterating until one vector—the dominant component of the motion—is identified. In some implementations, a new filter is generated every time new gestures are detected.

If the gesture-recognition module 248 is implemented as part of a specific application (such as a game or controller logic for a television), the database gesture record can also contain an input parameter corresponding to the gesture (which can be scaled using the scaling value); in generic systems where the gesture-recognition module 248 is implemented as a utility available to multiple applications, this application-specific parameter is omitted: when an application invokes the gesture-recognition module 248, it interprets the identified gesture according in accordance with its own programming.

In one implementation, the gesture-recognition module 248 breaks up and classifies one or more gestures into a plurality of gesture primitives. Each gesture can include or correspond to the path traversed by an object, such as user's hand or any other object (e.g., an implement such as a pen or paintbrush that the user holds), through 3D space. The path of the gesture can be captured by the cameras 102, 104 in conjunction with gesture-recognition module 248, and represented in the memory 208 as a set of coordinate (x, y, z) points that lie on the path, as a set of vectors, as a set of specified curves, lines, shapes, or by any other coordinate system or data structure. Any method for representing a 3D path of a gesture on a computer system is within the scope of the technology disclosed.

Each primitive can be a curve, such as an arc, parabola, elliptic curve, or any other type of algebraic or other curve. The primitives can be two-dimensional curves and/or three-dimensional curves. In one implementation, a gesture-primitives module includes a library of gesture primitives and/or parameters describing gesture primitives. The gesture-recognition module 248 can search, query, or otherwise access the gesture primitives by applying one or more parameters (e.g., curve size, shape, and/or orientation) of the detected path (or segment thereof) to the gesture-primitives module, which can respond with one or more closest-matching gesture primitives.

3D Solid Hand Model

Gesture-recognition system 106 not only can recognize gestures for purposes of providing input to the electronic device, but can also capture the position and shape of the user's hand 114 in consecutive video images in order to characterize a hand gesture in 3D space and reproduce it on the display screen 202. A 3D model of the user's hand is determined from a solid hand model covering one or more capsule elements built from the images using techniques described below with reference to FIGS. 3A-3F.

Figure 3A:
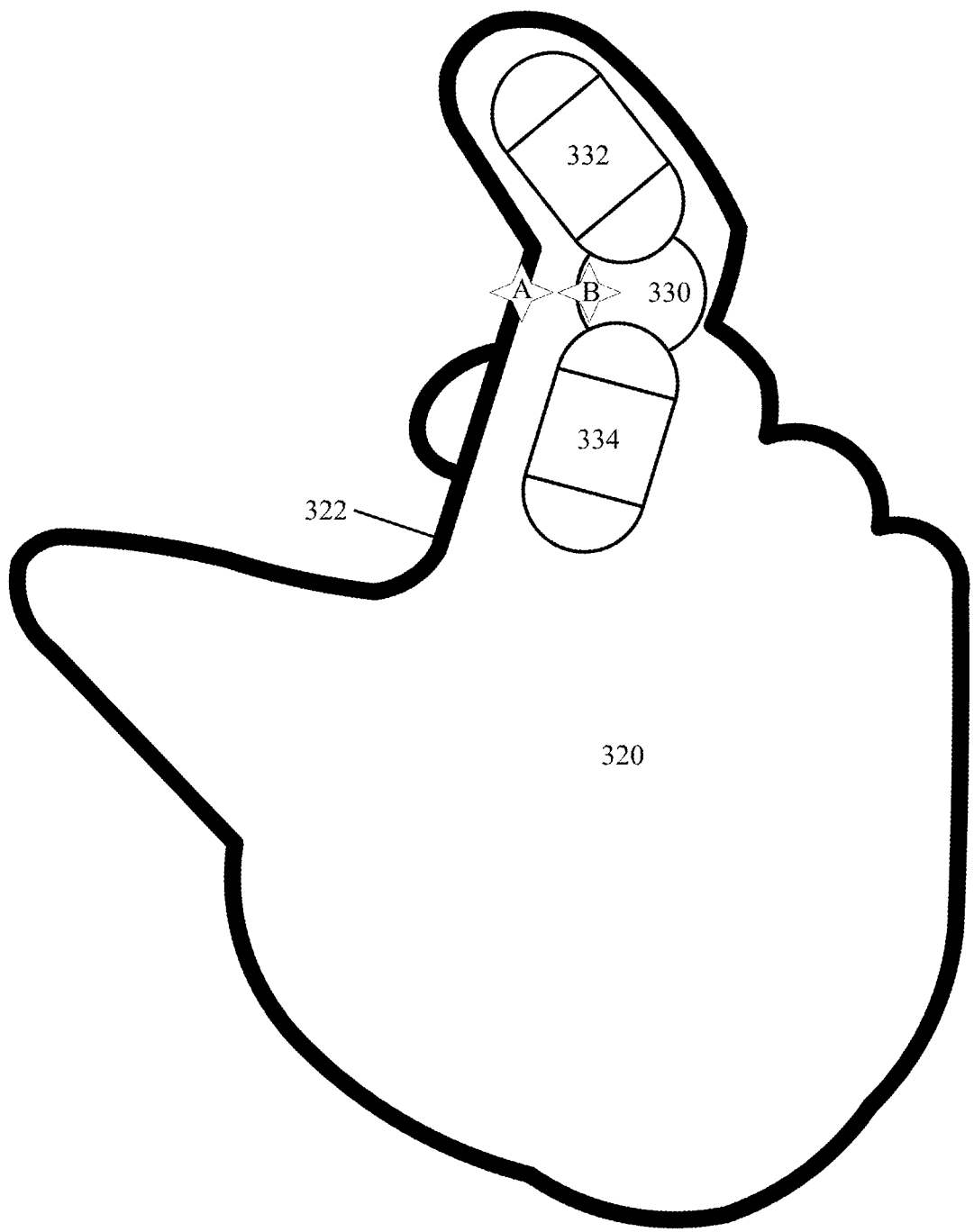
FIG. 3A shows one implementation of a 3D solid model hand with capsule representation of predictive information of a hand.

FIG. 3A shows one implementation of a 3D solid hand model 300A with capsule representation of predictive information of the hand 114. Examples of predictive information of the hand include finger segment length, distance between finger tips, joint angles between fingers, and finger segment orientation. As illustrated by FIG. 3A, the prediction information can be constructed from one or more model subcomponents referred to as capsules 330, 332, and 334, which are selected and/or configured to represent at least a portion of a surface of the hand 114 and virtual surface portion 322. In some implementations, the model subcomponents can be selected from a set of radial solids, which can reflect at least a portion of the hand 114 in terms of one or more of structure, motion characteristics, conformational characteristics, other types of characteristics of hand 114, and/or combinations thereof. In one implementation, radial solids are objects made up of a 2D primitive (e.g., line, curve, plane) and a surface having a constant radial distance to the 2D primitive. A closest point to the radial solid can be computed relatively quickly. As used herein, three or greater capsules are referred to as a "capsoodle."

One radial solid implementation includes a contour and a surface defined by a set of points having a fixed distance from the closest corresponding point on the contour. Another radial solid implementation includes a set of points normal to points on a contour and a fixed distance therefrom. In one implementation, computational technique(s) for defining the radial solid include finding a closest point on the contour and the arbitrary point, then projecting outward the length of the radius of the solid. In another implementation, such projection can be a vector normal to the contour at the closest point. An example radial solid (e.g., 332, 334) includes a "capsuloid," i.e., a capsule shaped solid including a cylindrical body and semi-spherical ends. Another type of radial solid (e.g., 330) includes a sphere. Different types of radial solids can be identified based on the foregoing teaching in other implementations.

One or more attributes can define characteristics of a model subcomponent or capsule. Attributes can include e.g., sizes, rigidity, flexibility, torsion, ranges of motion with respect to one or more defined points that can include endpoints in some examples. In one implementation, predictive information about the hand 114 can be formed to include a 3D solid model 300A of the hand 114 together with attributes defining the model and values of those attributes.

In some implementations, when the hand 114 morphs, conforms, and/or translates, motion information reflecting such motion(s) is included as observed information about the motion of the hand 114. Points in space can be recomputed based on the new observation information. The model subcomponents can be scaled, sized, selected, rotated, translated, moved, or otherwise re-ordered to enable portions of the model corresponding to the virtual surface(s) to conform within the set of points in space.

Figure 3B:
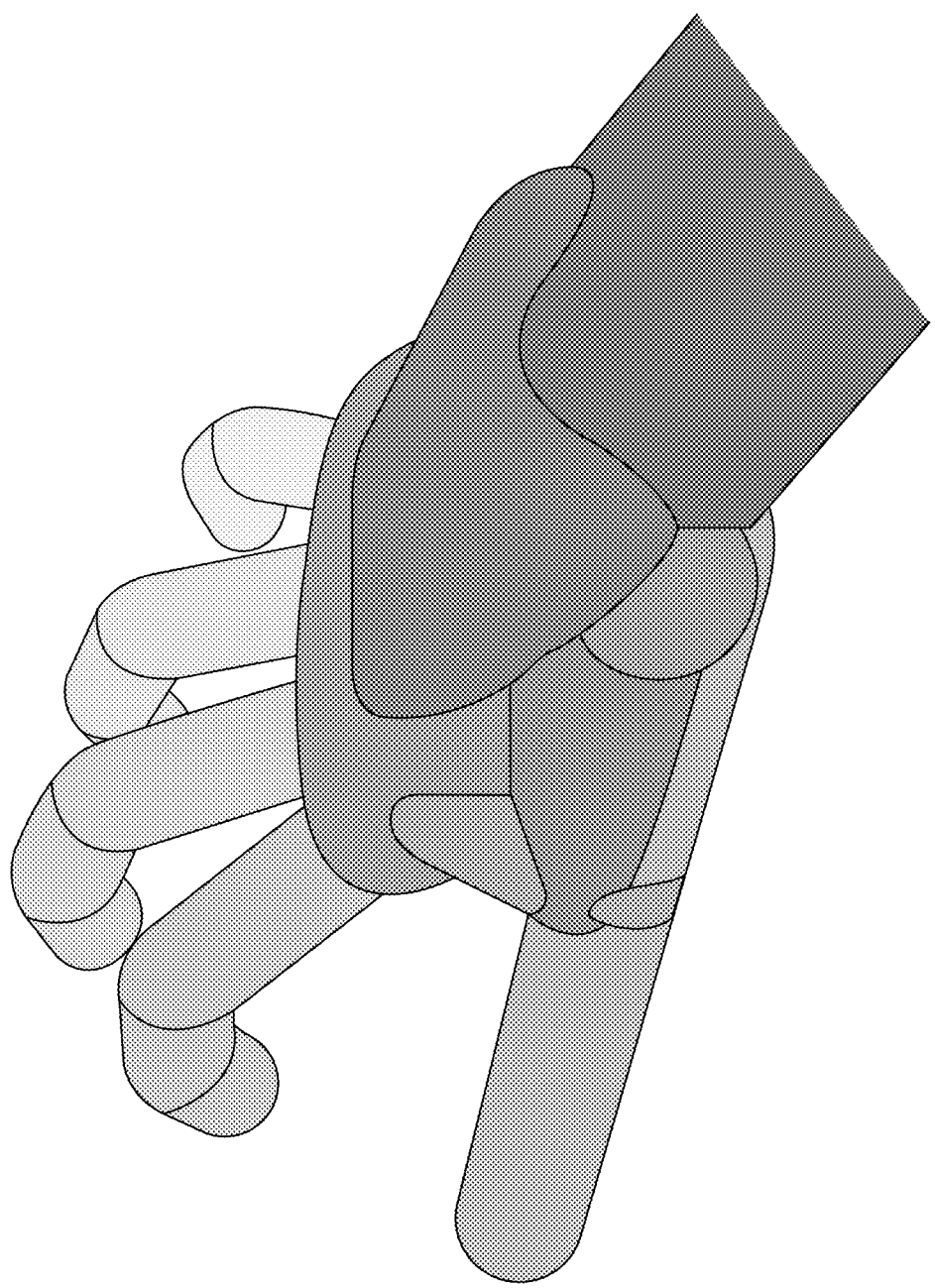
FIGS. 3B and 3C illustrate different views of a 3D capsule hand according to one implementation of the technology disclosed.
Figure 3C:
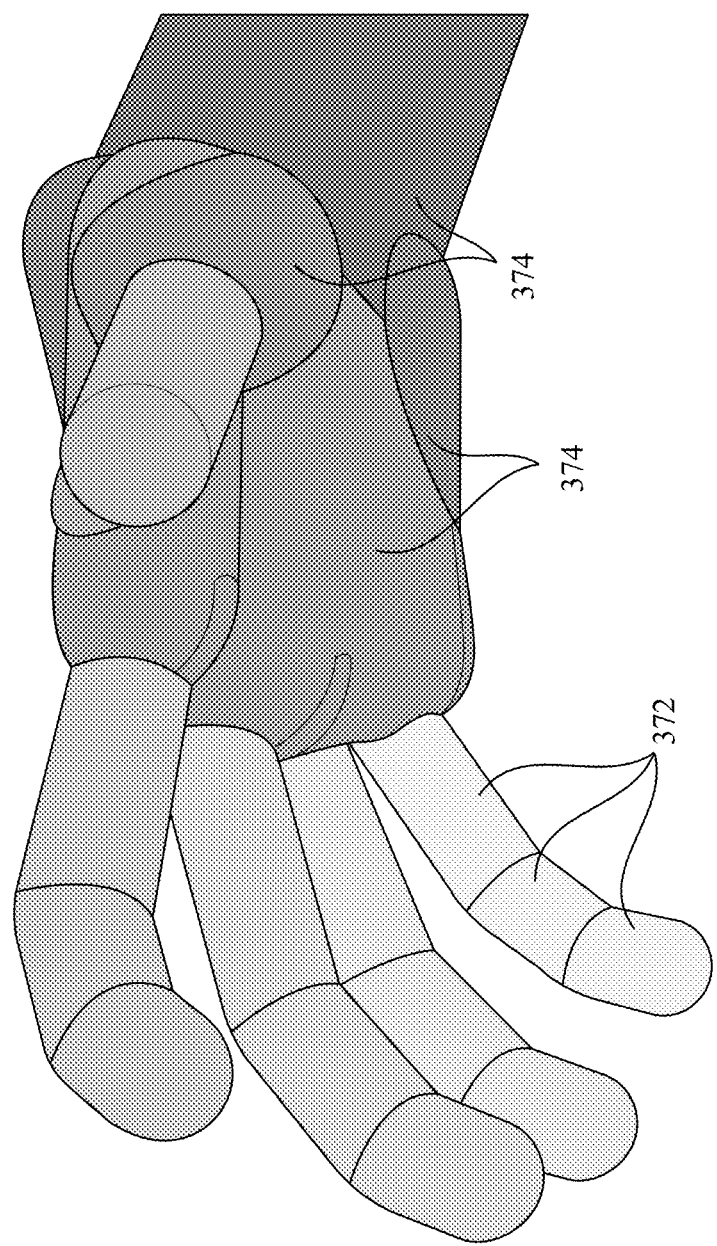
Figure 3D:
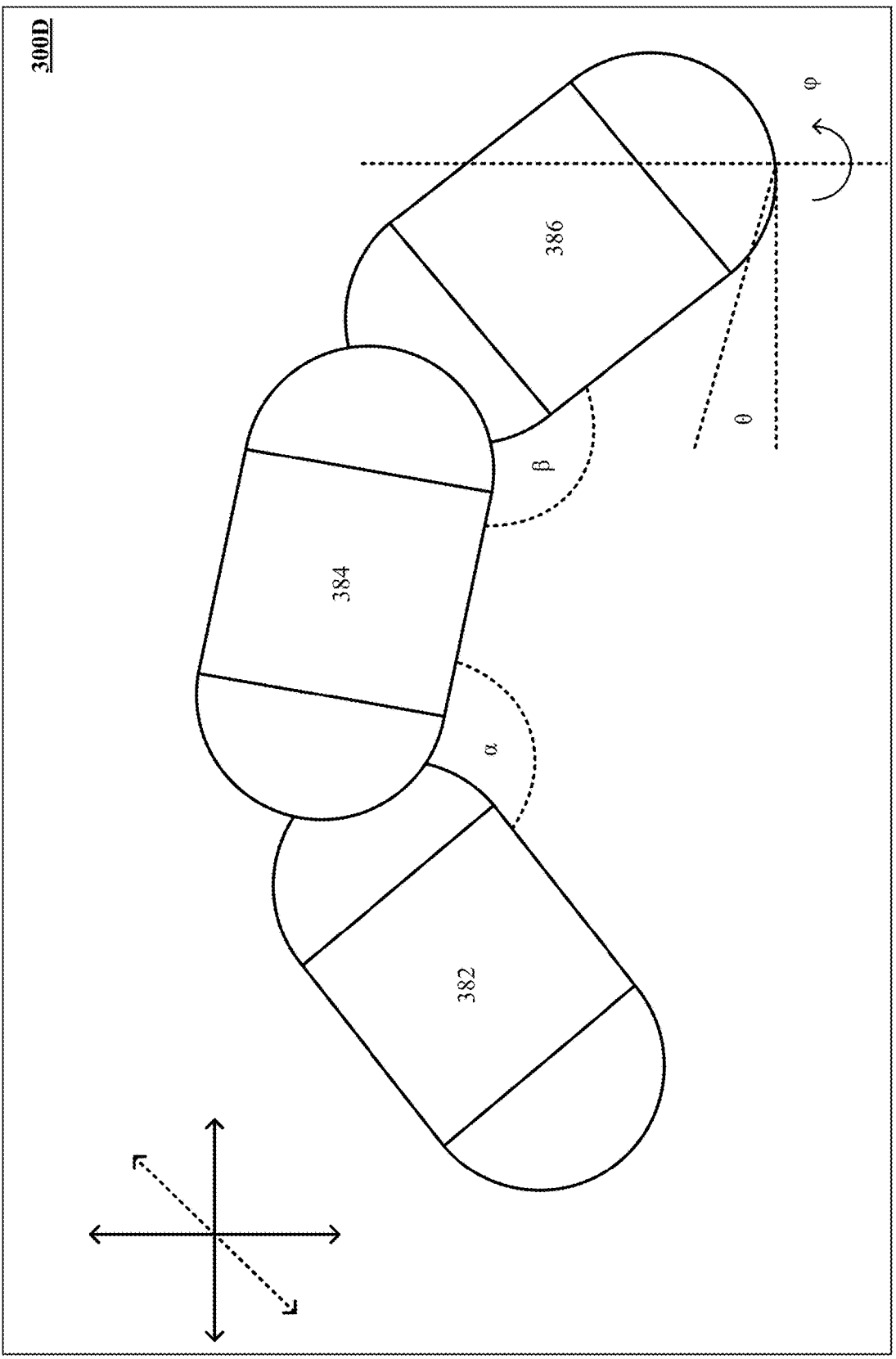
FIG. 3D depicts one implementation of generating a 3D finger capsuloid of a hand with different joint angles.

In one implementation and with reference to FIGS. 3B and 3C, a collection of radial solids and/or capsuloids can be considered a "capsule hand." In particular, FIGS. 3B and 3C illustrate different views 300B and 300C of a 3D capsule hand. A number of capsuloids 372, e.g. five (5), are used to represent fingers on a hand while a number of radial solids 374 are used to represent the shapes of the palm and wrist. With reference to FIG. 3D, a finger capsuloid 300C with radial solids 382, 384, and 386 can be represented by its two (2) joint angles ($\alpha$, $\beta$), pitch ($\theta$), and yaw ($\varphi$). In an implementation, the angle $\beta$ can be represented as a function of joint angle $\alpha$, pitch $\theta$, and yaw $\varphi$. Allowing angle $\beta$ to be represented this way can allow for faster representation of the finger capsuloid with fewer variables; see, e.g., U.S. Ser. No. 61/871,790, filed 28 Aug. 2013 and 61/873,758, filed 4 Sep. 2013. For example, one capsule hand can include five (5) capsules for each finger, a radial polygon defining a base of the hand, and a plurality of definitional capsules that define fleshy portions of the hand. In some implementations, the capsule hand 300B is created using stereo matching, depth maps, or by finding contours and/or feature points reduced to certain finite number of degrees of freedom sa shown in FIG. 3F, so as to enable simplification of problems of inverse kinematics (IK), sampling sizes, pose determination, etc.

Figure 3E:
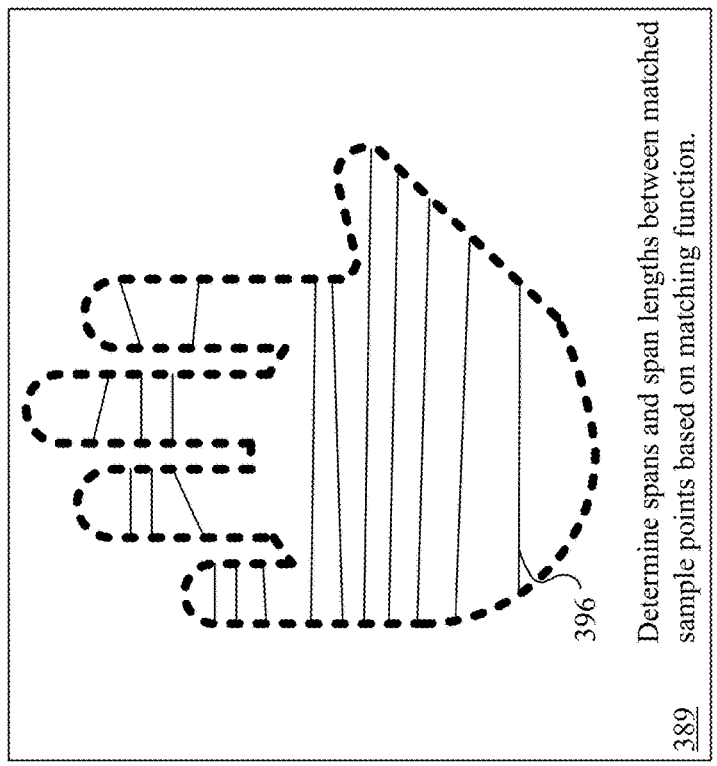
FIG. 3E is one implementation of determining spans and span lengths of a control object.
Figure 3E:
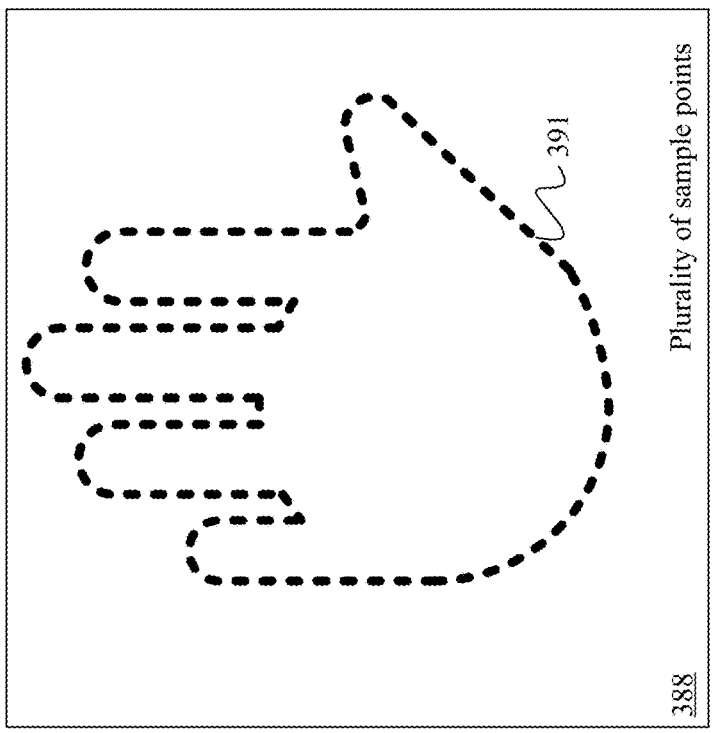
Figure 3E:
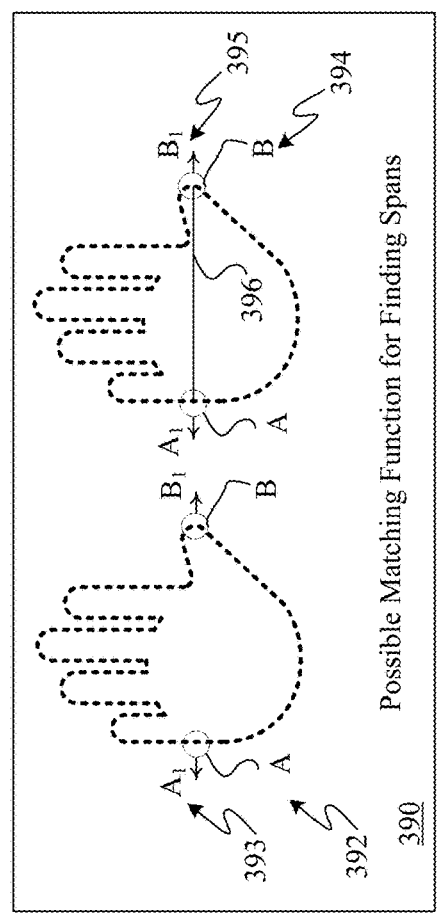

FIG. 3E depicts determination of spans and span lengths 300D in the observed information about the hand 114 in which one or more point pairings are selected from a surface portion as represented in the observed information. As illustrated by block 388 of FIG. 3E, an observed surface portion 391 (i.e., of observed information) can include a plurality of sample points from which one or more point pairings can be selected. In a block 390 of FIG. 3E, a point pairing between point A and point B of observed surface portion 391 are selected by application of a matching function. One method for determining a point pairing using a matching function is illustrated by FIG. 3E, in which a first unmatched (arbitrary) point A on a contour (of block 390 of FIG. 3E) representing a surface portion of interest in the observed information is selected as a starting point 392. A normal Ai 393 (of block 390 of FIG. 3E) is determined for the point A. A wide variety of techniques for determining a normal can be used in implementations, but in one example implementation, a set of points proximate to the first unmatched point, at least two of which are not co-linear, is determined. Then, a normal for the first unmatched point can be determined using the other points in the set by determining a normal perpendicular to the plane. For example, given points $P_1$, $P_2$, $P_3$, the normal n is given by the cross product:

$$n=(p_2-p_1)\times(p_3-p_1)_3$$

Another technique that can be used: (i) start with the set of points; (ii) form a first vector from $P_2-P_1$, (iii) apply rotation matrix to rotate the first vector 90 degrees away from the center of mass of the set of points. (The center of mass of the set of points can be determined by an average of the points). A yet further technique that can be used includes: (i) determine a first vector tangent to a point on a contour in a first image; (ii) determine from the point on the contour a second vector from that point to a virtual camera object in space; (iii) determine a cross product of the first vector and the second vector. The cross product is a normal vector to the contour.

Again with reference to FIG. 3E, the closest second unmatched point B 394 (of block 390 of FIG. 3E) reachable by a convex curve (line 396) having the most opposite normal $B_1$ 395 is found. Accordingly, points A and B form a point pairing. In FIG. 3E, a span length is determined for at least one of the one or more point pairings selected. Now with reference to block 389 of FIG. 3E, one or more spans and span lengths are determined for the one or more point pairings. In a representative implementation, a span can be found by determining a shortest convex curve for the point pairings A and B. It is determined whether the convex curve passes through any other points of the model. If so, then another convex curve is determined for paired points A and B. Otherwise, the span comprises the shortest continuous segment found through paired points A and B that only intersects the model surface at paired points A and B. In an implementation, the span can comprise a convex geodesic segment that only intersects the model at two points. A span can be determined from any two points using the equation of a line fitted to the paired points A and B for example.

Figure 3F:
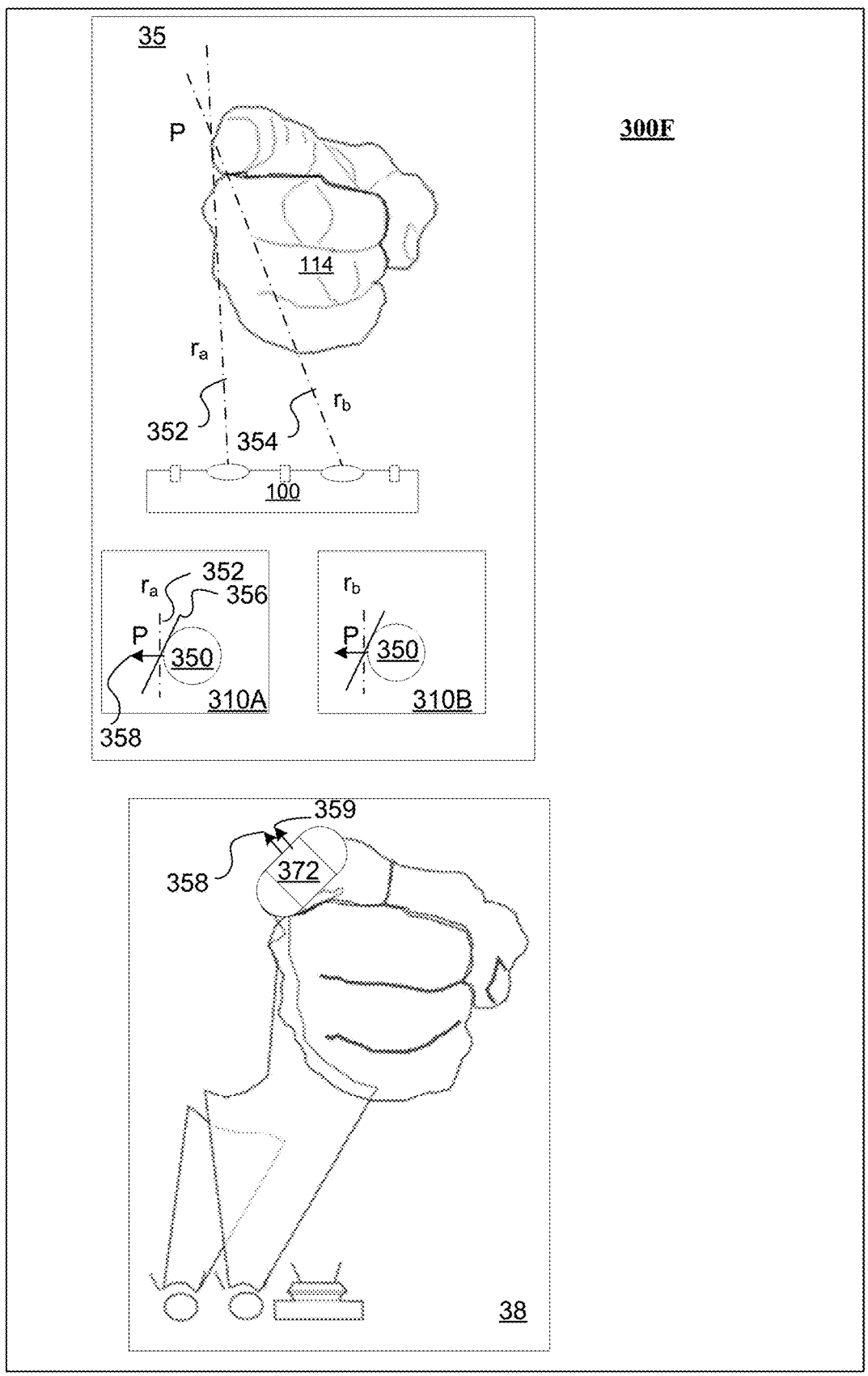
FIG. 3F illustrates one implementation of finding points in an image of an object being modeled.

FIG. 3F illustrates an implementation of finding points in an image of an object being modeled. Now with reference to block 35 of FIG. 3F, cameras 102, 104 are operated to collect a sequence of images (e.g., 310A, 310B) of the object 114. The images are time correlated such that an image from camera 102 can be paired with an image from camera 104 that was captured at the same time (or within a few milliseconds). These images are then analyzed by object detection module 228 that detects the presence of one or more objects 350 in the image, and object analysis module 238 analyzes detected objects to determine their positions and shape in 3D space. If the received images 310A, 310B include a fixed number of rows of pixels (e.g., 1080 rows), each row can be analyzed, or a subset of the rows can be used for faster processing. Where a subset of the rows is used, image data from adjacent rows can be averaged together, e.g., in groups of two or three.

Again with reference to block 35 in FIG. 3F, one or more rays 352 can be drawn from the camera(s) proximate to an object 114 for some points P, depending upon the number of vantage points that are available. One or more rays 352 can be determined for some point P on a surface of the object 350 in image 310A. A tangent 356 to the object surface at the point P can be determined from point P and neighboring points. A normal vector 358 to the object surface 350 at the point P is determined from the ray and the tangent by cross product or other analogous technique. In block 38, a model portion (e.g., capsule 387) can be aligned to object surface 350 at the point P based upon the normal vector 358 and a normal vector 359 of the model portion 372. Optionally, as shown in block 35, a second ray 354 is determined to the point P from a second image 310B captured by a second camera. In some instances, fewer or additional rays or constraints from neighboring capsule placements can create additional complexity or provide further information. Additional information from placing neighboring capsules can be used as constraints to assist in determining a solution for placing the capsule. For example, using one or more parameters from a capsule fit to a portion of the object adjacent to the capsule being placed, e.g., angles of orientation, the system can determine a placement, orientation and shape/size information for the capsule. Object portions with too little information to analyze can be discarded or combined with adjacent object portions.

Figure 4A:
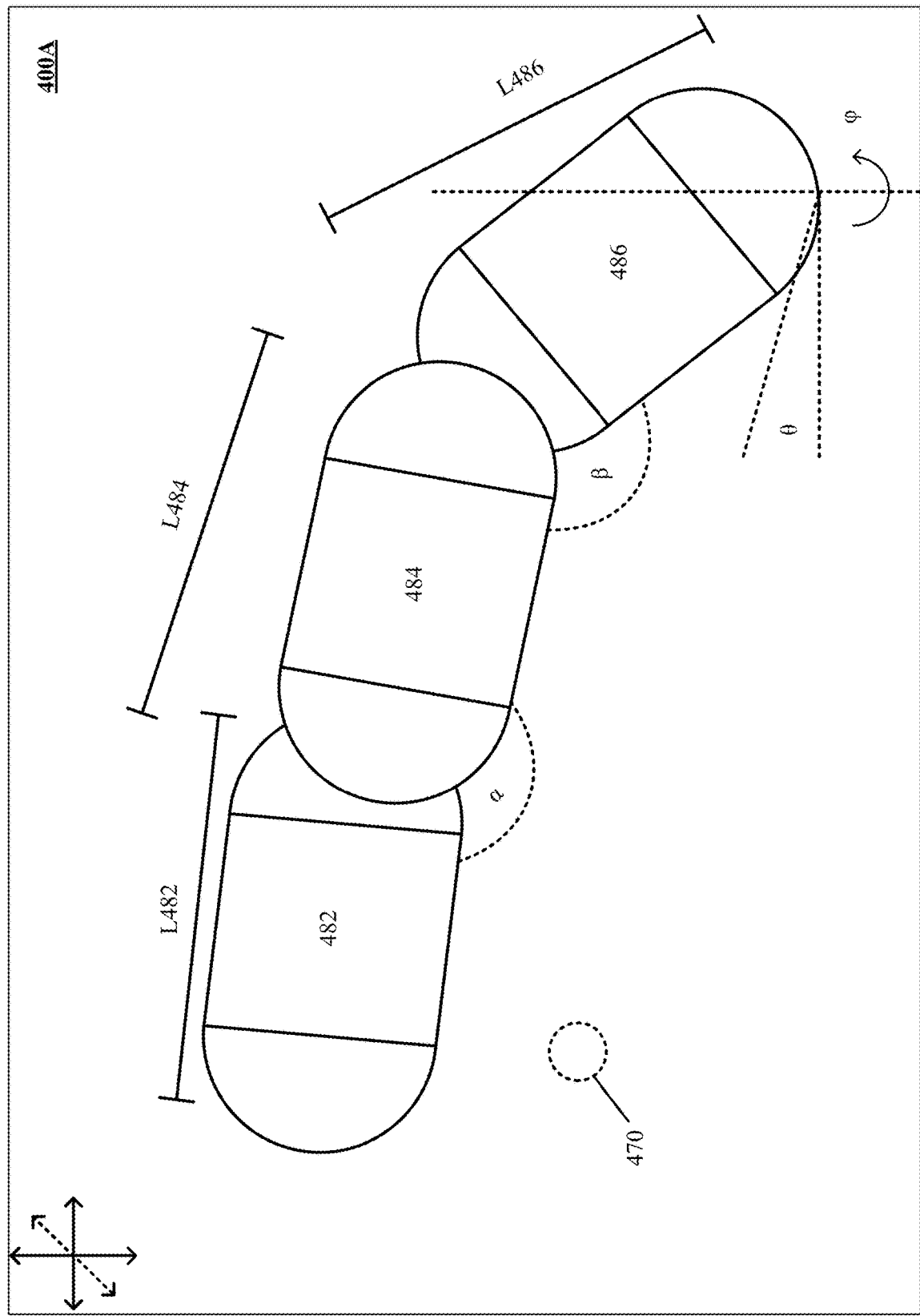
FIGS. 4A-4B are one implementation of determination and reconstruction of fingertip position of a hand.
Figure 4B:
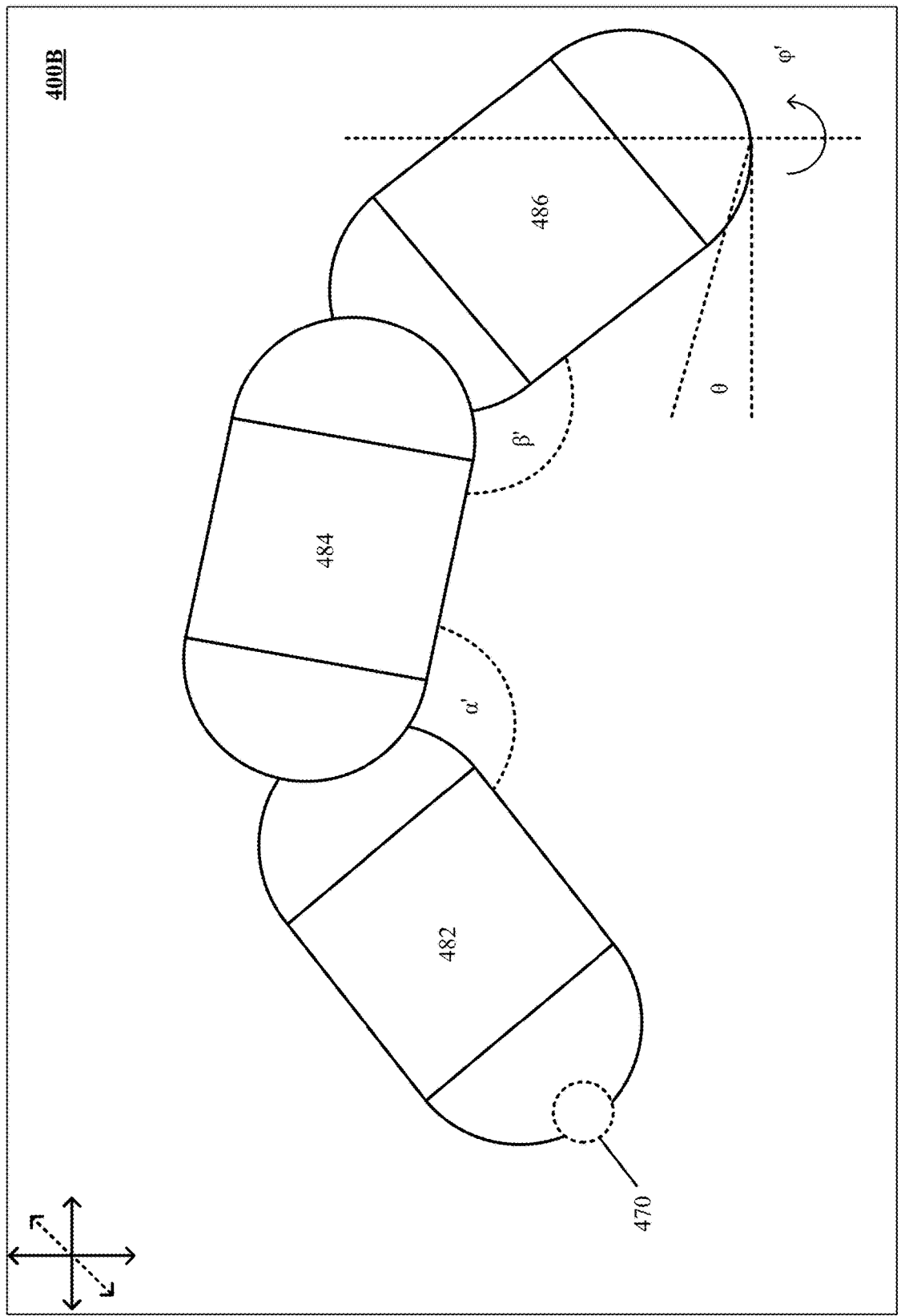

In one implementation, as illustrated by FIGS. 4A-4B, a fingertip position 400A-B can be determined from an image and can be reconstructed in 3D space. In FIG. 4A, a point 470 is an observed fingertip. Model 482, 484, and 486 are aligned such that the tip of 482 is coincident with the location in space of point 470 determined from the observed information. In one technique, angle $\alpha$ and angle $\beta$ are allowed to be set equal, which enables a closed form solution for $\theta$ and $\varphi$ as well as angle $\alpha$ and angle $\beta$.

$$s^2=2ac(-2a^2-2c^2+b^2-2a-2b-2c+4ac)+-2b^2(a^2+c^2)$$

$$\alpha=\beta=2\tan^{-1}s-(a+c)b$$

$$\varphi=x_1/\text{norm}(x)$$

$$\theta=x_2/\text{norm}(x)$$

Wherein norm(x) can be described as the norm of a 3D point x (470 in FIG. 4B) with a, b and c being capsule lengths L482, L484, L486 in FIG. 4A.

Figure 5:
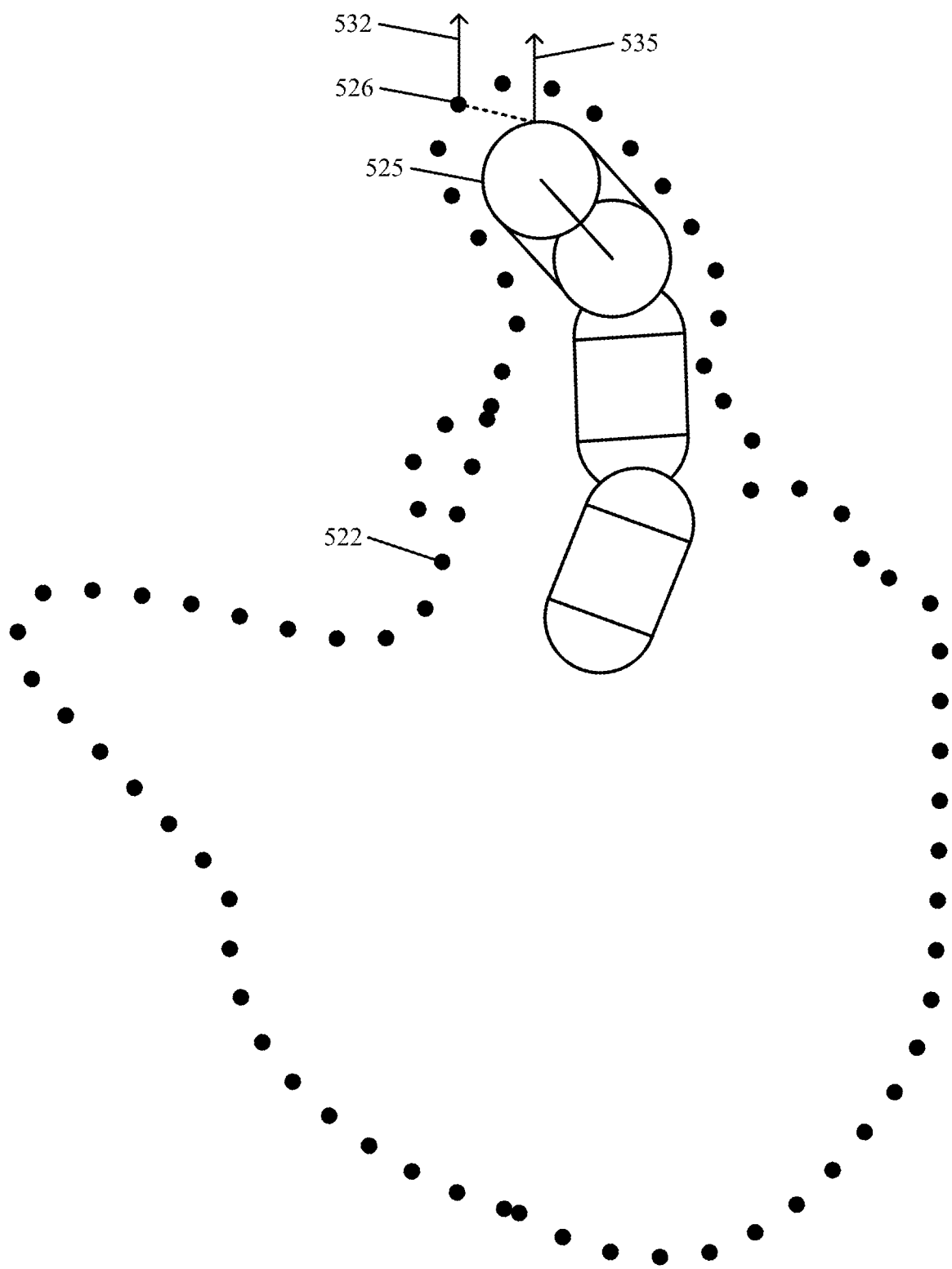
FIG. 5 shows one implementation of improving capsule representation of predictive information.

FIG. 5 illustrates one implementation of improving 500 capsule representation of predictive information. In one implementation, observation information 522 including observation of the control object (such as hand 114) can be compared against the 3D solid hand model at least one of periodically, randomly or substantially continuously (i.e., in real-time). Observational information 522 can include without limitation observed values of attributes of the control object corresponding to the attributes of one or more model subcomponents in the predictive information for the control object. In another implementation, comparison of the model 525 with the observation information 522 provides an error indication 526. In an implementation, an error indication 526 can be computed by first associating a set A of 3D points with a corresponding normal direction 532 to a set B of 3D points with a corresponding normal direction 535 on the subcomponents surface. The association can be done in a manner that assures that each paired point in set A and B has the same associated normal. An error can then be computed by summing the distances between each point in set A and B. This error is here on referred to the association error; see, e.g., U.S. Ser. No. 61/873,758, filed Sep. 4, 2013.

Predictive information of the 3D hand model can be aligned to the observed information using any of a variety of techniques. Aligning techniques bring model portions (e.g., capsules, capsuloids, capsoodles) into alignment with the information from the image source (e.g., edge samples, edge rays, interior points, 3D depth maps, and so forth). In one implementation, the model is rigidly aligned to the observed information using iterative closest point (ICP) technique. The model can be non-rigidly aligned to the observed information by sampling techniques.

One ICP implementation includes finding an optimal rotation R and translation T from one set of points A to another set of points B. First each point from A is matched to a point in set B. A mean square error is computed by adding the error of each match:

$$\text{MSE}=\text{sqrt}(\Sigma(R^*x_i+T-y_i)^{\prime*}(R^*x_i+T-y_i))$$

An optimal R and T can be computed and applied to the set of points A or B, in some implementations.

In order to enable the ICP to match points to points on the model, a capsule matching technique can be employed. One implementation of the capsule matcher includes a class that "grabs" the set of data and computes the closest point on each tracked hand (using information like the normal). Then the minimum of those closest points is associated to the corresponding hand and saved in a structure called "Hand Data." Other points that don't meet a minimal distance threshold can be marked as unmatched.

In some implementations, rigid transformations and/or non-rigid transformations can be composed. One example composition implementation includes applying a rigid transformation to predictive information. Then an error indication can be determined, and an error minimization technique such as described herein above can be applied. In an implementation, determining a transformation can include calculating a rotation matrix that provides a reduced RMSD (root mean squared deviation) between two paired sets of points. One implementation can include using Kabsch Algorithm to produce a rotation matrix. The Kabsch algorithm can be used to find an optimal rotation R and translation T that minimizes the error:

$$\text{RMS}=\text{sqrt}(\Sigma(R^*x_i+T-y_i)^{\prime*}(R^*x_i+T-y_i))$$

The transformation (both R and T) are applied rigidly to the model, according to one implementation. The capsule matching and rigid alignment can be repeated until convergence. In one implementation, the Kabsch can be extended to ray or co-variances by the following minimizing:

$$\Sigma(R^*x_i+T-y_i)^{\prime*}M_i^*(R^*x_i+T-y_i)$$

In the equation above, $M_i$ is a positive definite symmetric matrix. In other implementations and by way of example, one or more force lines can be determined from one or more portions of a virtual surface.

One implementation applies non-rigidly alignment to the observed by sampling the parameters of each finger. A finger is represented by a 3D vector where the entry of each vector is Pitch, Yaw and Bend of the finger. The Pitch and Yaw can be defined trivially. The bend is the angle between the first and second Capsule and the second and third Capsule which are set to be equal. The mean of the samples weighted by the RMS is taken to be the new finger parameter. After Rigid Alignment all data that has not been assigned to a hand, can be used to initialize a new object (hand or tool).

In another implementation, predictive information can include collision information concerning two or more capsuloids. By means of illustration, several possible fits of predicted information to observed information can be removed from consideration based upon a determination that these potential solutions would result in collisions of capsuloids.

In some implementations, a relationship between neighboring capsuloids, each having one or more attributes (e.g., determined minima and/or maxima of intersection angles between capsuloids) can be determined. In an implementation, determining a relationship between a first capsuloid having a first set of attributes and a second capsuloid having a second set of attributes includes detecting and resolving conflicts between first attribute and second attributes. For example, a conflict can include a capsuloid having one type of angle value with a neighbor having a second type of angle value incompatible with the first type of angle value. Attempts to combine a capsuloid with a neighboring capsuloid having attributes, such that the combination can exceed what is allowed in the observed information or to pair incompatible angles, lengths, shapes, or other such attributes, can be removed from the predicted information without further consideration, according to one implementation.

In one implementation, raw image information and fast lookup table can be used to find a look up region that gives constant time of computation of the closest point on the contour given a position. Fingertip positions are used to compute point(s) on the contour which can be then determined whether the finger is extended or non-extended, according to some implementations. A signed distance function can be used to determine whether points lie outside or inside a hand region, in another implementation. An implementation includes checking to see if points are inside or outside the hand region.

In another implementation, a variety of information types can be abstracted from the 3D solid model of a hand. For example, velocities of a portion of a hand (e.g., velocity of one or more fingers, and a relative motion of a portion of the hand), state (e.g., position, an orientation, and a location of a portion of the hand), pose (e.g., whether one or more fingers are extended or non-extended, one or more angles of bend for one or more fingers, a direction to which one or more fingers point, a configuration indicating a pinch, a grab, an outside pinch, and a pointing finger), and whether a tool or object is present in the hand can be abstracted in various implementations.

Gesture Data Representation

Motion data representing free-form gestures performed using a control object can be stored as data units called frames. Frames include information necessary to capture the dynamic nature of the free-form gestures, referred to as "feature sets." Hands and pointables (fingers and tools) are examples of feature sets of a gesture that are described by features directly related to real attributes of the hands and pointables. For instance, a hand can be described by three dimensional values, like: position of center of hand, normal vector, and direction vector pointing from the center to the end of fingers. Similarly, fingers or tools (which are linger and thinner than fingers) can described by a set of features including a position of tip, pointing direction vector, length, and width.

Figure 6A:
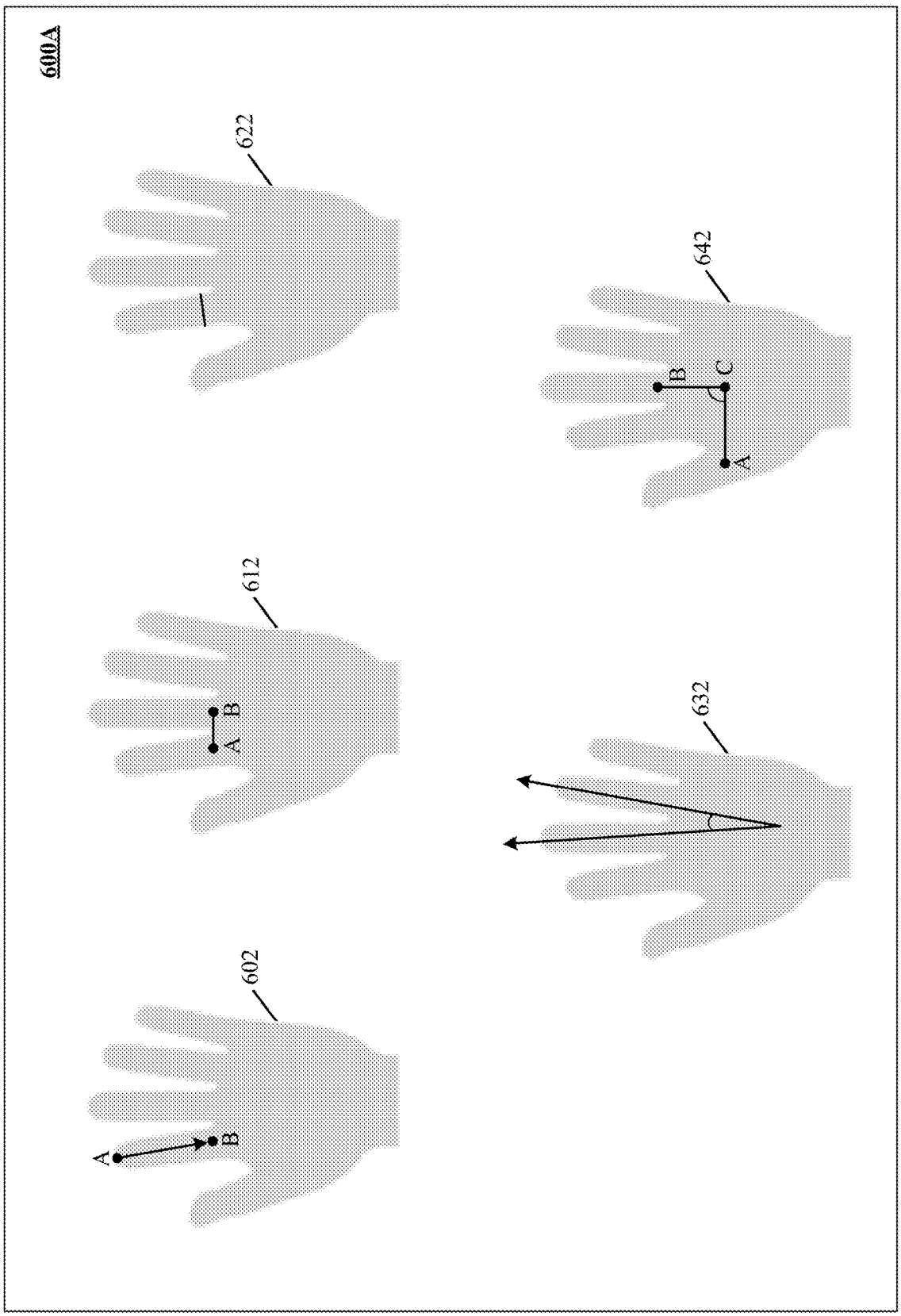
FIG. 6A depicts one implementation of feature sets of a free-form gesture that are described by features directly related to real attributes of a control object.

As illustrated in FIG. 6A, several different features of a hand can be determined such that a first feature set can include numbers of fingers in a frame, Euclidean distances between consecutive finger's tips, and absolute angles between consecutive fingers. In another implementation, a second feature can be the first feature set extended by the distances between consecutive finger tips and the position of the hand's palm. In yet another implementation, a third feature set can include features from the second feature set extended by the five angles between fingers and normal of hand's palm.

In one implementation, distance between two nearest base points of a finger is calculated by multiplying a reversed normalized direction vector designated to a finger base point with the length of the finger. Further, the beginning of this vector is placed in the fingertip position and the end of the vector identifies the finger base point, as shown in silhouette 602. Silhouette 612 is an example of distance between two nearest base points of fingers. Silhouette 622 is an implementation depicting the ration of a finger's thickness to the maximal finger's thickness.

According to an implementation presented as silhouette 632, angles between two nearest fingers are determined by calculating the angle between finger direction vectors of two consecutive fingers. In another implementation, angles between a particular finger and the first finger relative to palm position are calculated using two fingertip positions and a palm position. After this, the line segments between the palm position, fingertip positions, and the searched angle between two finger segments are identified, as shown in silhouette 642.

In some implementations, a feature set can include features encoding the information about the speed of the hand during a free-form gesture. In one implementation, a recorded displacement of the hand in a rectangular or curvilinear coordinate system can be determined. In one implementation, an object detection module 228 expresses the changing locations of the hand as it traverses a path through a monitored space in Cartesian/(x, y, z) coordinates. According to some implementations, a gestural path of a control object can be entirely defined by its angles in the relative curvilinear coordinates. In one example, if C is a vector representing the control object in the Cartesian coordinate system as C(x, y, z)=(initial point-final point) (x, y, z). Then, transformation to a curvilinear coordinate system can be denoted as C(ρ, θ, φ), where ρ represents the radius of a curve, θ is the azimuth angle of the curve, and φ is the inclination angle of the curve.

The object detection module 228 identifies these coordinates by analyzing the position of the object as captured in a sequence of images. A filtering module receives the Cartesian coordinates, converts the path of the object into a Frenet-Serret space, and filters the path in that space. In one implementation, the filtering module then converts the filtered Frenet-Serret path back into Cartesian coordinates for downstream processing by other programs, applications, modules, or systems.

Frenet-Serret formulas describe the kinematic properties of a particle moving along a continuous, differentiable curve in 3D space. A Frenet-Serret frame is based on a set of orthonormal vectors, which illustrates a path of an object (e.g., a user's hand, a stylus, or any other object) through the monitored space; points are the (x, y, z) locations of the object as identified by the object detection module 228. The filtering module attaches a Frenet-Serret frame of reference to a plurality of locations (which can or may not correspond to the points) on the path. The Frenet-Serret frame consists of (i) a tangent unit vector (T) that is tangent to the path (e.g., the vector T points in the direction of motion), (ii) a normal unit vector (N) that is the derivative of T with respect to an arclength parameter of the path divided by its length, and (iii) a binormal unit vector (B) that is the cross-product of T and N. Alternatively, the tangent vector can be determined by normalizing a velocity vector (as explained in greater detail below) if it is known at a given location on the path. These unit vectors T, N, B collectively form the orthonormal basis in 3D space known as a TNB frame or Frenet-Serret frame. The Frenet-Serret frame unit vectors T, N, B at a given location can be calculated based on a minimum of at least one point before and one point after the given location to determine the direction of movement, the tangent vector, and the normal vector. The binormal vector is calculated as the cross-product of the tangent and normal vectors. Any method of converting the path represented by the points to Frenet-Serret frames is within the scope of the technology disclosed.

Once a reference Frenet-Serret frame has been associated with various points along the object's path, the rotation between consecutive frames can be determined using the Frenet-Serret formulas describing curvature and torsion. The total rotation of the Frenet-Serret frame is the combination of the rotations of each of the three Frenet vectors described by the formulas $$\frac{dT}{ds} = \kappa N, \frac{dN}{ds} = -\kappa T + \tau B, \text{ and}$$

$$\frac{dB}{ds} = -\tau N,$$

where $$\frac{d}{ds}$$

is the derivative with respect to arc length, κ is the curvature, and τ is the torsion of the curve. The two scalars κ and τ can define the curvature and torsion of a 3D curve, in that the curvature measures how sharply a curve is turning while torsion measures the extent of its twist in 3D space. Alternatively, the curvature and torsion parameters can be calculated directly from the derivative of best-fit curve functions (i.e., velocity) using, for example, the equations $$\kappa = \frac{|\vec{v} \times \vec{a}|}{|\vec{v}|^3} \text{ and } \tau = \frac{(\vec{v} \times \vec{a}) \cdot \vec{a}'}{|\vec{v} \times \vec{a}|^2}.$$

Figure 6B:
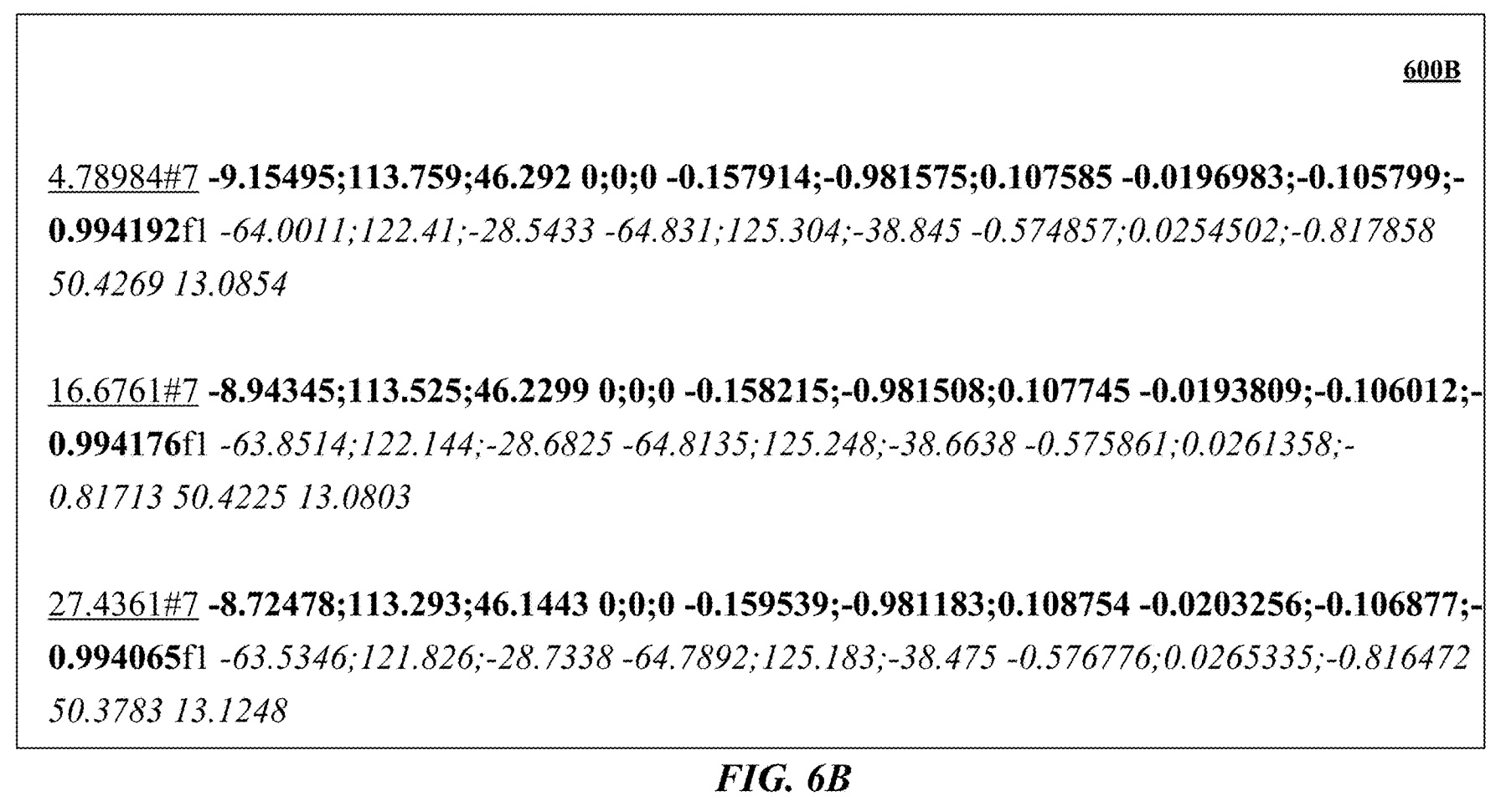

The sequence shown in FIG. 6B is an example representation of gestural data captured for one or more free-form gestures performed using a hand. In the sequence 600B, each line represents a frame and each frame includes a timestamp and hand parameters such as hand id, palm position, stabilized palm position, palm normal, vector, palm direction vector, and detected fingers parameters. Further, the finger parameters include finger id, fingertip position, stabilized tip position, finger direction vector, finger length, and finger width. Again with reference to sequence 600B, underlined text depicts frame timestamp, the bold faced data highlights information about the hand, and the italicized alphanumeric characters identify information about the fingers.

Actuator

Actuator 258 of FIG. 2 serves as a microcontroller that acts as an interpreter between the gestural commands and the robotic commands. In one implementation, actuator 258 is a hardware application-programming interface (API) that directly controls the robotic arm with n degrees of freedom in joint motion by converting signals carrying motion data into corresponding 8-bit digital values. In some implementations, actuator 258 sends the converted digital values through the UART line to the robotic arm. In the case of a remote robotic arm, a client software implementing the gesture-recognition module 248 can send the signals of control commands to the server that controls the remote robotic arm. In other implementations, actuator 258 generates the actuating signals that drive the motors of the robotic arm. In yet another implementation, the actuator 258 includes a signal amplifier that boosts low frequency actuating signals. In some other implementation, the actuator 258 includes a signal filter that reduces noise by separating high frequency actuating signals.

Actuator 258 can include ports to interface with the gesture-recognition module 248 and receive motion data. After processing the motion data, actuator 258 can send it to the robotic arm over one or more networks, including any one or any combination of a LAN (local area network), WAN (wide area network), telephone network (Public Switched Telephone Network (PSTN), Session Initiation Protocol (SIP), 3G, 4G LTE), wireless network, point-to-point network, star network, token ring network, hub network, WiMAX, WiFi, peer-to-peer connections like Bluetooth, Near Field Communication (NFC), Z-Wave, ZigBee, or other appropriate configuration of data networks, including the Internet. In other implementations, other networks can be used such as an intranet, an extranet, a virtual private network (VPN), or a non-TCP/IP based network.

Figure 7A:
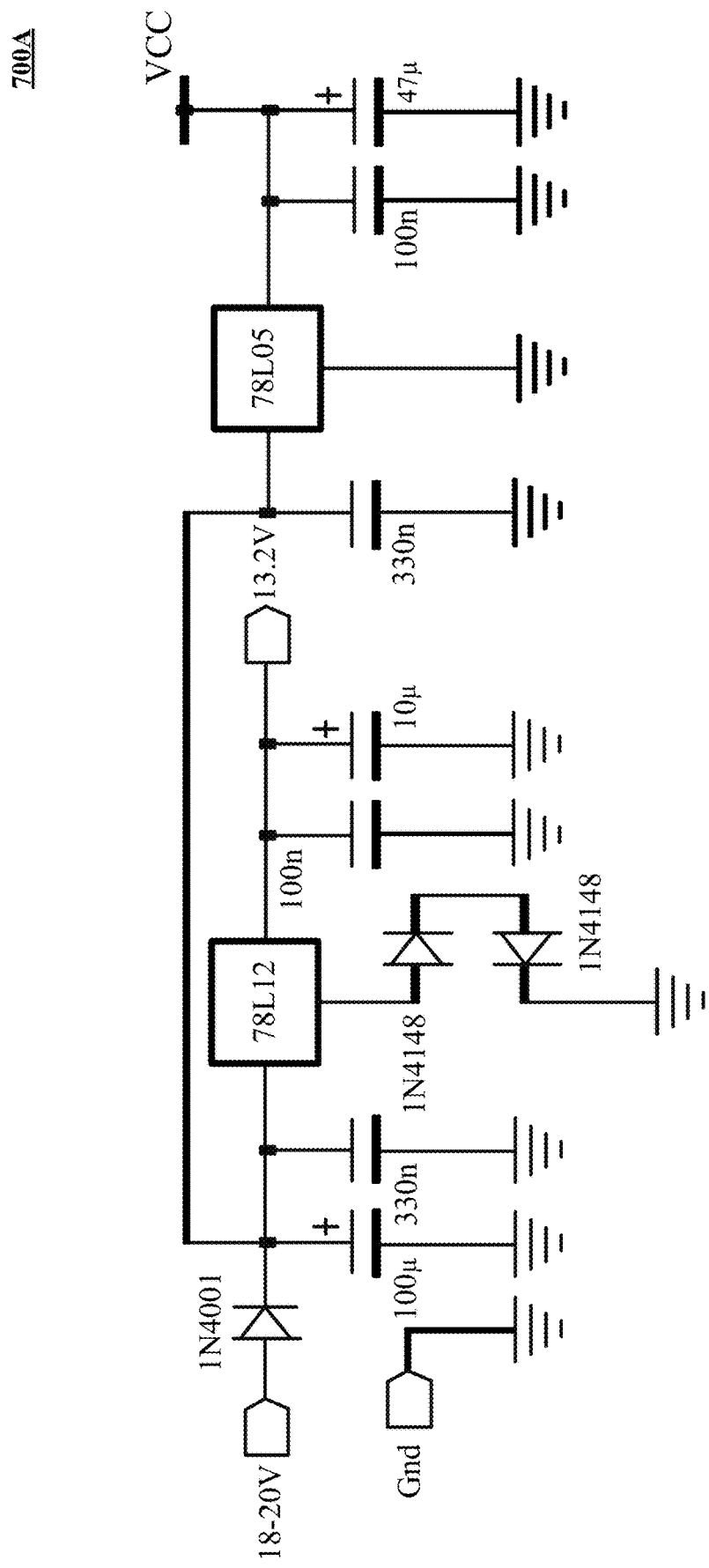
FIGS. 7A and 7B illustrate a circuitry of an actuator in communication with a robotic arm.
Figure 7B:
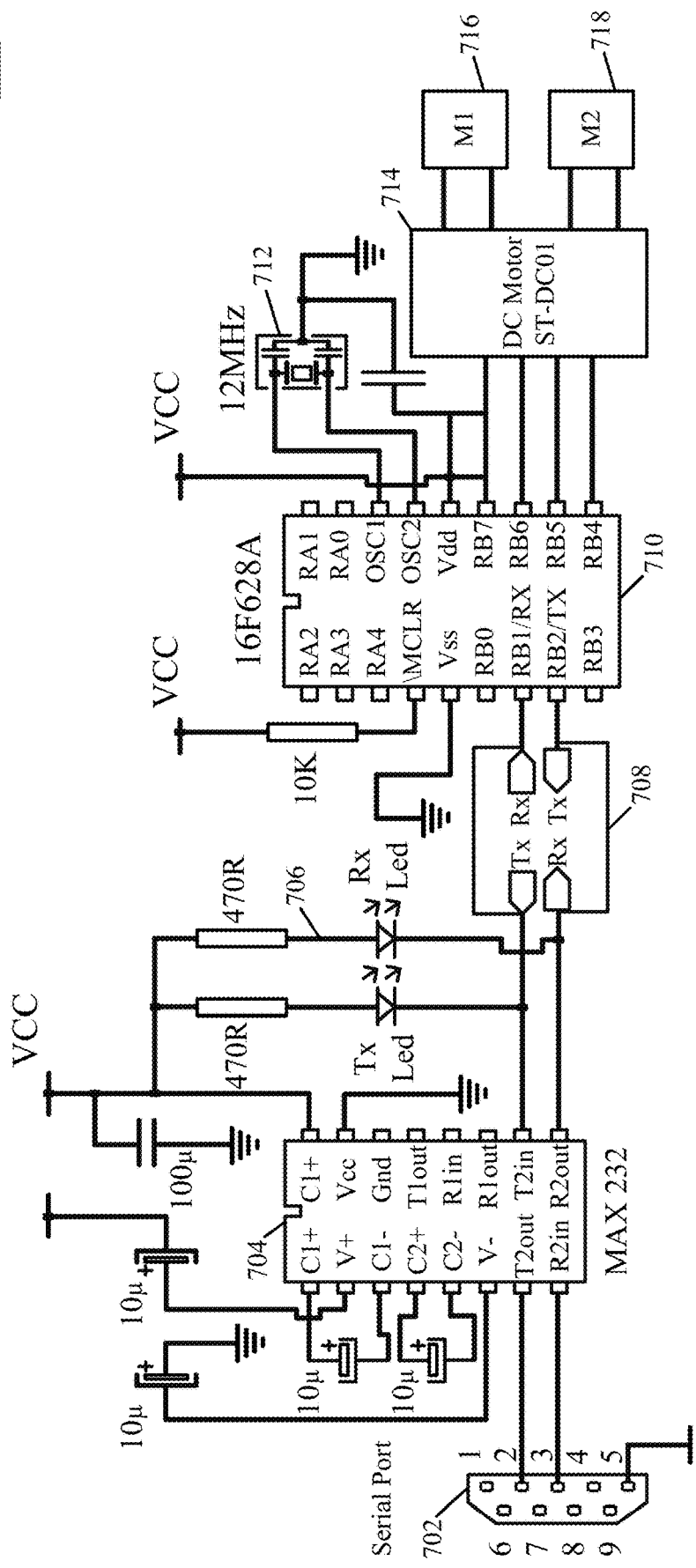

FIGS. 7A and 7B illustrate a circuitry 700A of the actuator 258 in communication with a robotic arm. According to one implementation, actuator 258 can be connected to the robotic arm through serial link, with circuitry 700A being the power source. In FIG. 7B, MAX 232 is a voltage level shifter integrated circuit (IC) 704. The o/p circuit can operate in 3.3V to 5V and the serial port 702 can operate in voltage level of ±15V, in one implementation. Tx and Rx are represented as a closed loop circuit 708 in between I/P and O/P components, which facilitate serial data transmission. Further, an opto-isolator 706 can be used for isolating the I/P and O/P components, in some implementations. In addition, a 12 Mz crystal oscillator 712 can be used to generate constant frequency of oscillation for PIC 16F628A. Signals carrying motion data can be transmitted from the gesture-recognition module 248 as I/P to PIC 710, which generates corresponding O/P that are forwarded to the DC motor driving circuitry 714 via port RB7 to RB4 to effectuate the motors M1 716 and M2 718 of the robotic arm.

Human-Robot Interface

Figure 8:
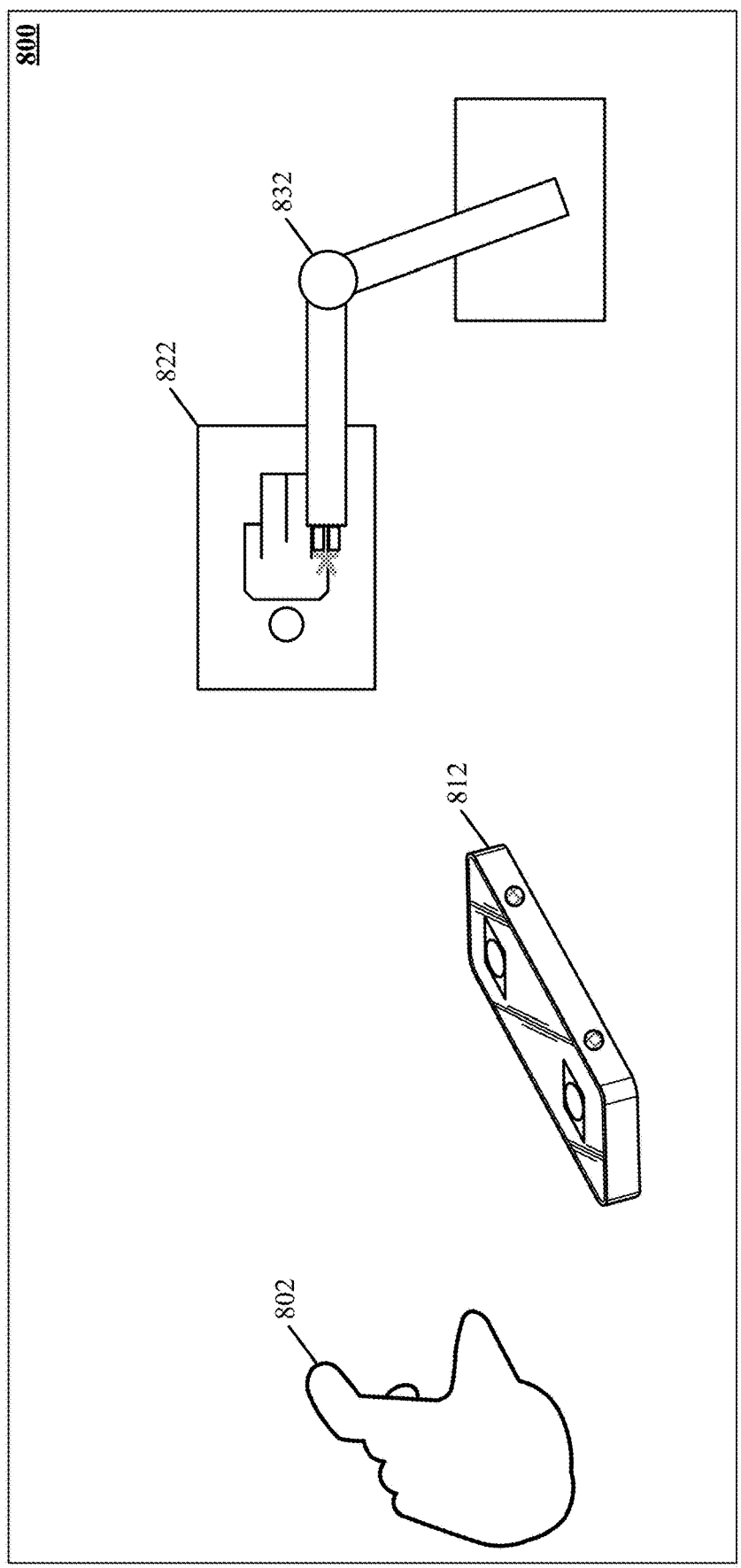
FIG. 8 illustrates one implementation of using free-form gestures to manipulate a workpiece by a robotic tool.

FIG. 8 illustrates one implementation of using 800 free-form gestures 802 to manipulate a workpiece 822 by a robotic tool 832. Free-form gestures are captured in a 3D sensory space using a motion sensory control device 812. Further, the gestures 802 are translated into robotic tool commands that produce smoothed emulating motions by the robotic tool 832 by recognizing a gesture segment within the gestures 802 that represents physical contact between the robotic tool 832 and a workpiece 822 and applying a force to the workpiece 822 through the robotic tool 832. In one example, when the hand 802 performs a scooping gesture, then the robotic tool 832 emulates and replicates the scooping gesture of the same or different scale. In other examples, gesture emulation, replication, and translation can include any one or combination of pinching gestures, clenching gestures, hovering gestures, pointing gestures, or grasping gestures.

Figure 9:
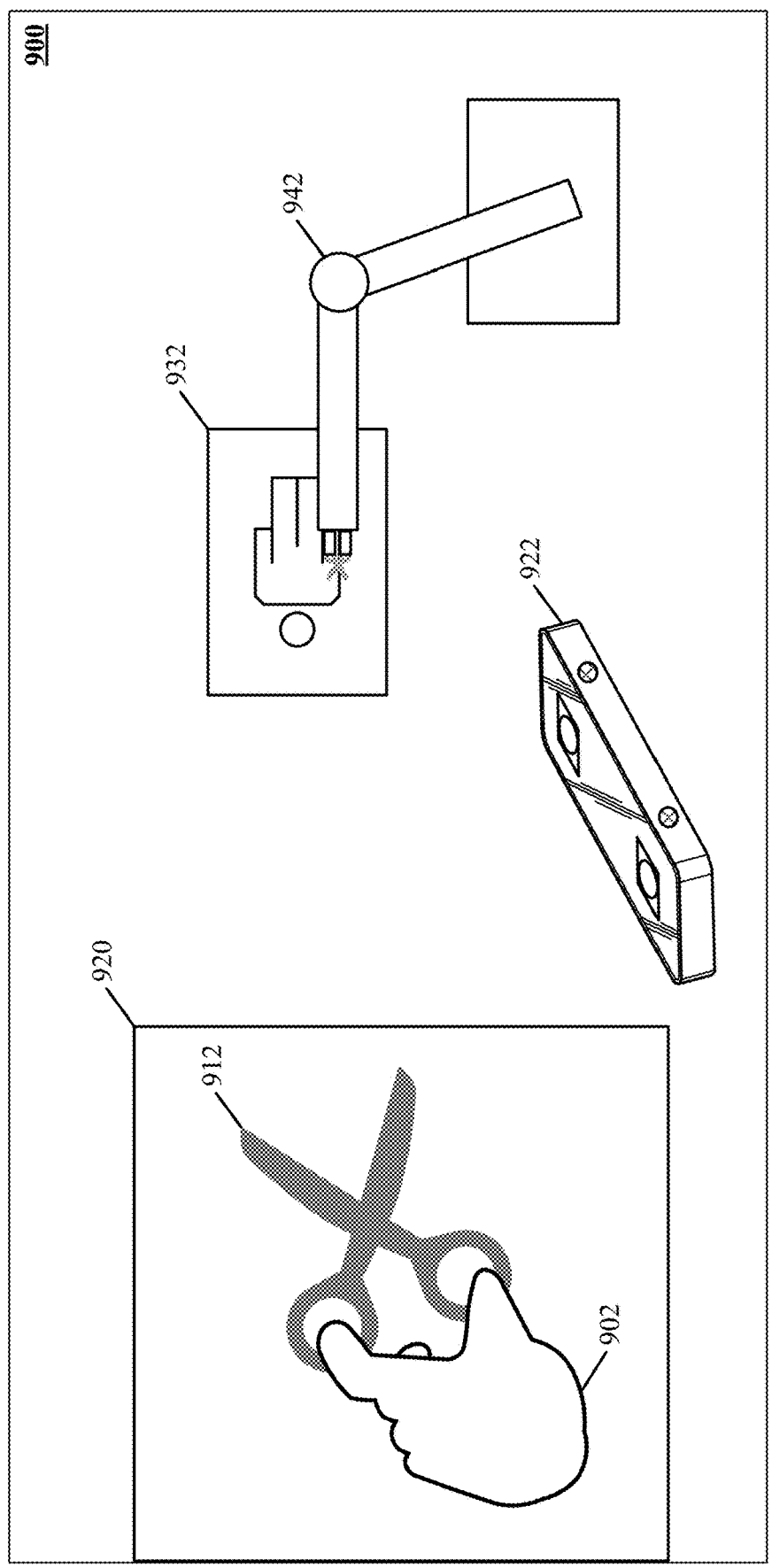
FIG. 9 is one implementation of using interaction between free-form gestures and a manipulable object to control interaction of a robotic tool with a workpiece.

FIG. 9 is one implementation of using 900 interaction between free-form gestures 902 and a manipulable object 912 to control interaction of a robotic tool 942 with a workpiece 932. As shown in FIG. 9, a gesture of a hand 902 and interaction 920 of the gesture with a manipulable object such as scissor 912 in a 3D sensory space using a motion sensory control device 922. Further, the gesture and the interaction 920 is translated into robotic tool commands that produce smoothed emulating actions performed by a robotic tool 942 on a workpiece 932 by recognizing a gesture segment within the interaction 920 that represents physical contact between the robotic tool 942 and the workpiece 932 and applying a force to the workpiece 932 through the robotic tool 942.

Figure 10:
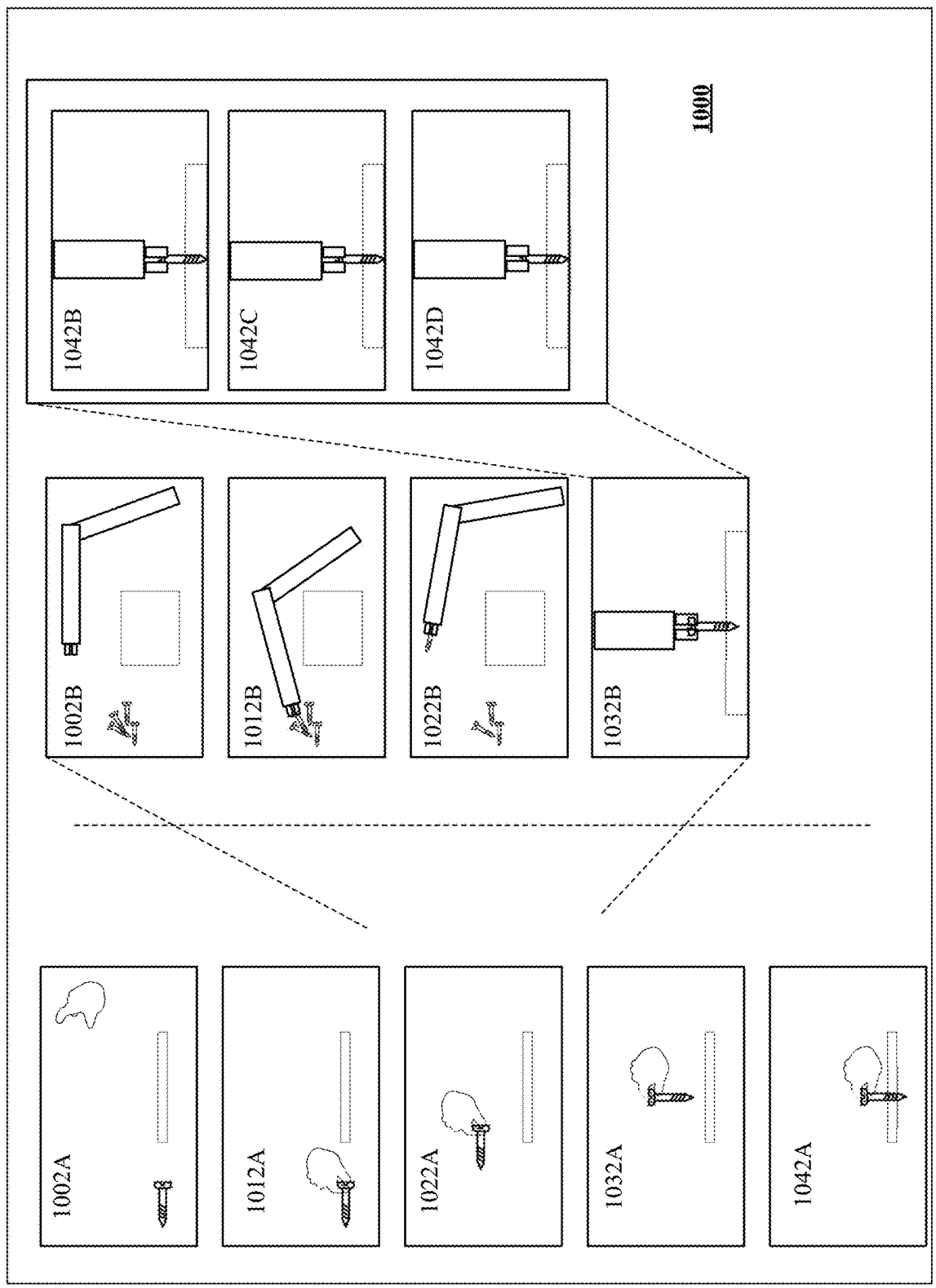
FIG. 10 illustrates one implementation of controlling manipulation of a real target objet though a robotic tool responsive to interactions between a control object and a dummy target object.

FIG. 10 illustrates an industrial implementation of controlling 1000 manipulation of a real target objet though a robotic tool responsive to interactions between a control object and a dummy target object. In the example show in FIG. 10, block 1002A shows a hand as a control object that interacts with a dummy screw and block 1002B includes a robotic tool and one or more real screws. When the hand picks the dummy screw in block 1012A, the robotic tool grabs the real screws in block 1012B responsive to the interaction in block 1012A. Similarly, the interactions between the hand and dummy screw in blocks 1022A, 1032A, and 1042A cause emulated manipulations of the real screws by the robotic tool in corresponding blocks 1022B, 1032B, 1042B, 1042C, and 1042D.

Figure 11:
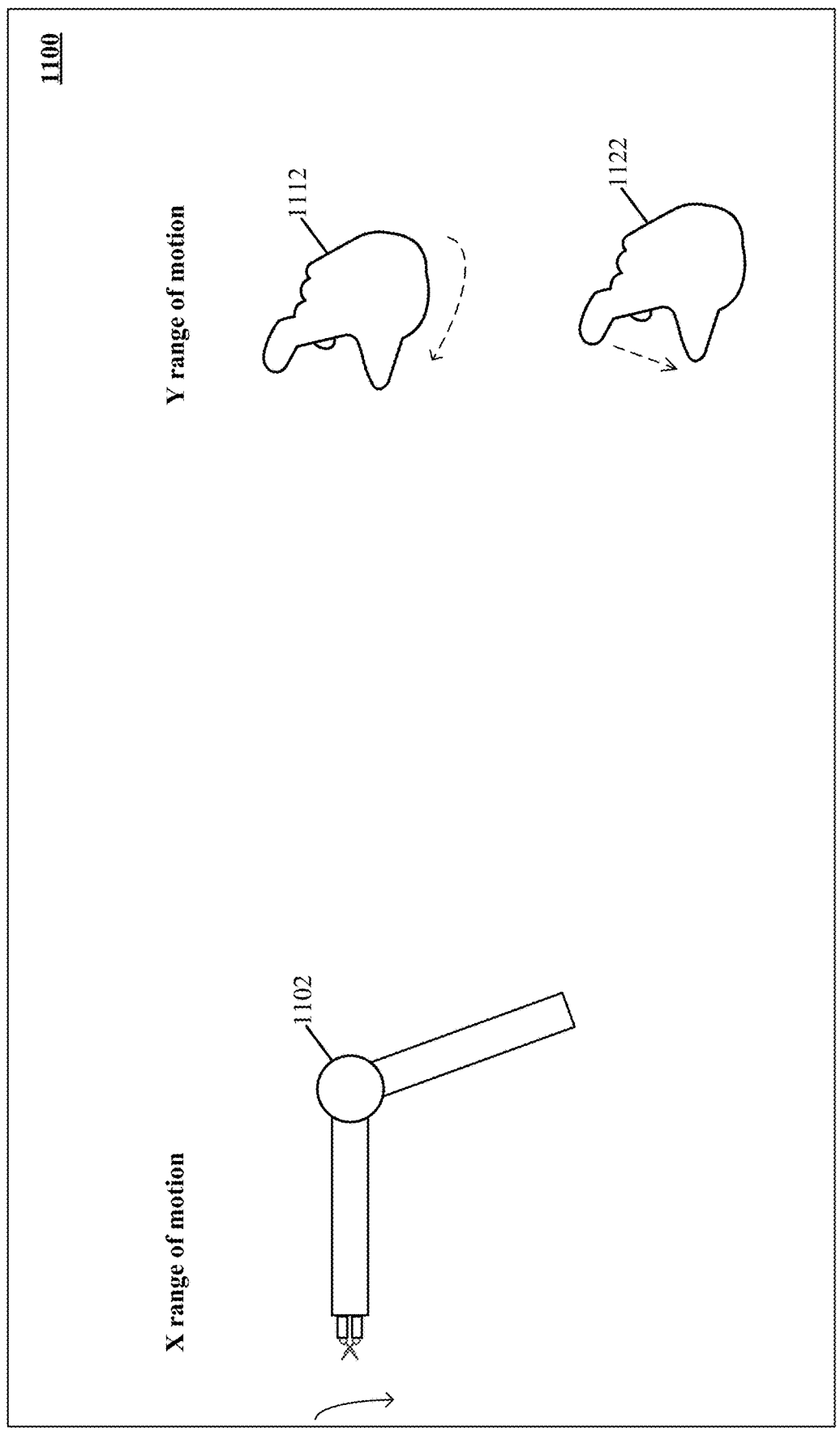
FIG. 11 shows one implementation of interpreting a maximum value of a parameter of robotic tool actuation in response to an extreme degree of motion of a control object.

FIG. 11 shows one implementation of interpreting a maximum value of a parameter of robotic tool actuation in response to an extreme degree of motion of a control object. According to some implementations, parameters of robotic tool actuation include at least one of path, trajectory, velocity, angular velocity, orientation, Euler angles, roll, pitch, and yaw angles, torque, torsion, stress, shear, strain of the robotic tool during the smoothed emulating motions. In one implementation, the maximum value of the parameter is an amplification function of the extreme degree of motion. In another implementation, the maximum value of the parameter is a polynomial function of the extreme of motion. In some other implementation, the maximum value of the parameter is a transcendental function of the extreme of motion. In yet another implementation, the parameter is a step function of the extreme of motion. In the example shown in FIG. 11, a Y range of circular motion of a grab gesture 1112 or pinch gesture 1122 of a hand is translated into X range of circular motion of the robotic tool 1102. For instance, if the hand's natural limit of circular motion is 270°, then the responsive robotic tool actuation is an amplified circular motion of 340°.

Figure 12:
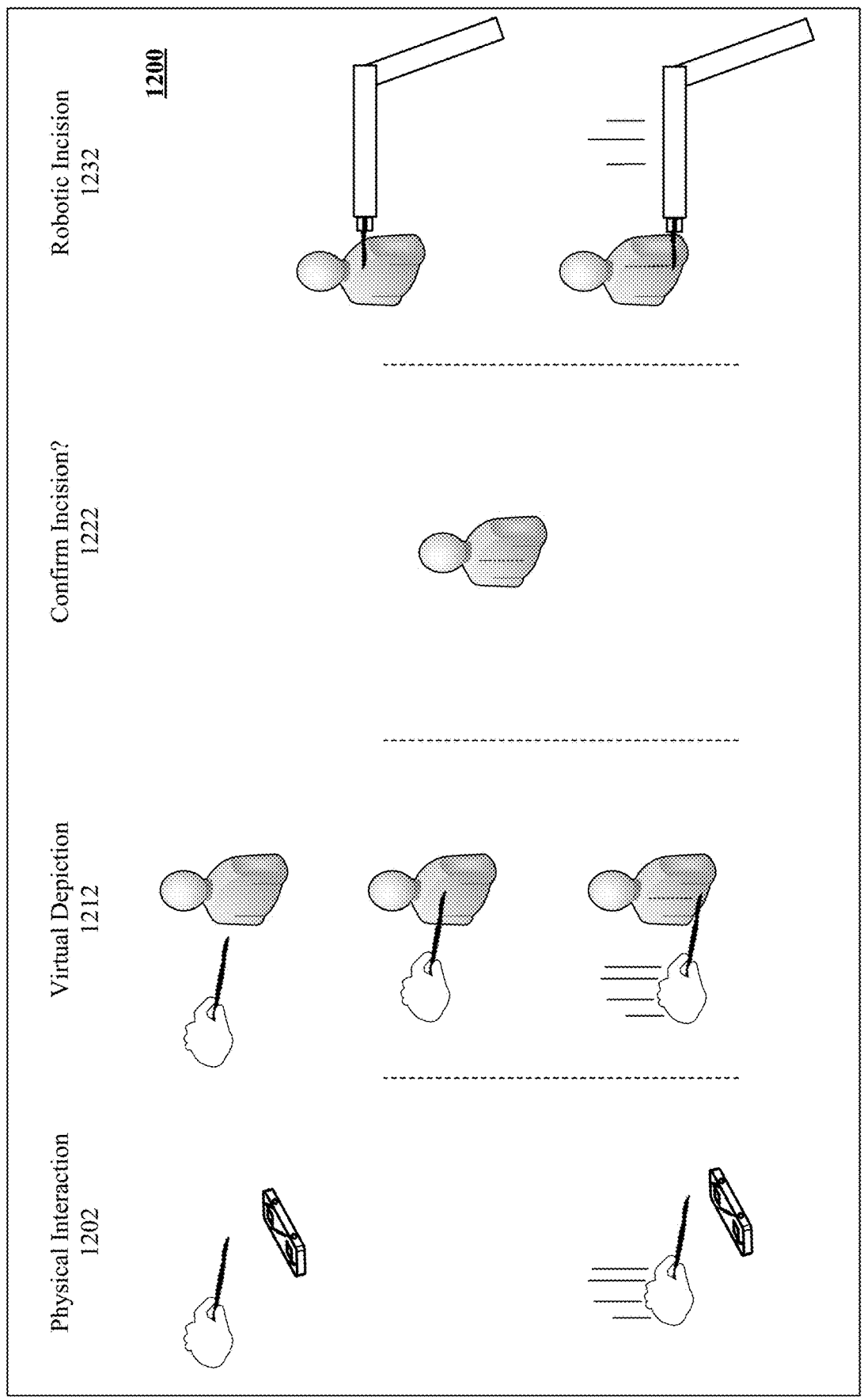
FIG. 12 shows one implementation of using interaction between free-form gestures and a stationary target object to control interaction of a robotic tool with a workpiece.

FIG. 12 shows a medical implementation of using interaction 1200 between free-form gestures and a stationary target object to control interaction of a robotic tool with a workpiece. In particular, FIG. 12 shows one implementation of performing a surgical procedure using free-form gestures 1202 that interact with a virtual dummy object at action 1212. In some implementations, a visual depiction of the virtual contact is generated for display to the manipulator so that the manipulator can confirm or reject the actual performance of the gesture on a real target object at action 1222, based on the rendered virtual consequences depicted prior to the actual performance by a robotic tool at action 1232. In one example, a surgeon can see the virtual results of the incision he has performed on a dummy patient before the incision is actually performed on a real patient by a robotic arm. In other implementations, haptographic feedback resulting from the performed gestures can be provided to the manipulator so as to aid in the manipulator's understanding of the impact of the gestures; see, e.g., Haptography: Capturing and Recreating the Rich Feel of Real Surfaces, the entire disclosure of which is hereby incorporated by reference.

Some Particular Implementations

The methods described in this section and other sections of the technology disclosed can include one or more of the following features and/or features described in connection with additional methods disclosed. In the interest of conciseness, the combinations of features disclosed in this application are not individually enumerated and are not repeated with each base set of features. The reader will understand how features identified in this section can readily be combined with sets of base features identified as implementations such as pervasive introduction, gesture recognition system, computer system, 3D solid hand model, gesture data representation, actuator, human-robot interface, etc.

These methods can be implemented at least partially with a database system, e.g., by one or more processors configured to receive or retrieve information, process the information, store results, and transmit the results. Other implementations may perform the actions in different orders and/or with different, fewer or additional actions than those discussed. Multiple actions can be combined in some implementations. For convenience, these methods is described with reference to the system that carries out a method. The system is not necessarily part of the method.

Other implementations of the methods described in this section can include a non-transitory computer readable storage medium storing instructions executable by a processor to perform any of the methods described above. Yet another implementation of the methods described in this section can include a system including memory and one or more processors operable to execute instructions, stored in the memory, to perform any of the methods described above.

Some example implementations are listed below with certain implementations dependent upon the implementation to which they refer to:

1. A method of using free-form gestures to manipulate a workpiece by a robotic tool, the method including:
capturing free-form gestures in a three-dimensional (3D) sensory space and translating the gestures into robotic tool commands that produce smoothed emulating motions by a robotic tool, including:
recognizing a gesture segment within the gestures that represents physical contact between the robotic tool and a workpiece; and
determining a command to the robotic tool to apply a force to the workpiece, wherein a magnitude of the force is based on a parameter of the gesture segment.

2. The method of implementation 1, further including capturing edge information for fingers of a hand that performs the free-form gestures and computing finger positions of a 3D solid hand model for the hand during the free-form gestures.

3. The method of implementation 1, further including capturing edge information for a palm of a hand that performs the free-form gestures and computing palm positions of a 3D solid hand model for the hand during the free-form gestures.

4. The method of implementation 1, further including capturing finger segment length information for fingers of a hand that performs the free-form gestures and initializing a 3D solid hand model for the hand.

5. The method of implementation 1, further including capturing joint angle and segment orientation information of a hand that performs the free-form gestures and applying the joint angle and segment orientation information to a 3D solid hand model for the hand during the free-form gestures.

6. The method of implementation 2, 3, 4, and 5, further including:
using the 3D hand model to capture a curling of the hand during the free-form gestures; and
interpreting the curling as a parameter of robotic tool translation.

7. The method of implementation 6, further including:
using the 3D hand model to detect the curling as an extreme degree of motion of the hand during the free-form gestures; and
responsive to the detecting, interpreting a maximum value of a parameter of robotic tool actuation.

8. The method of implementation 7, wherein the maximum value of the parameter is an amplification function of the extreme degree of motion.

9. The method of implementation 7, wherein the maximum value of the parameter is a polynomial function of the extreme of motion.

10. The method of implementation 7, wherein the maximum value of the parameter is a transcendental function of the extreme of motion.

11. The method of implementation 7, wherein the maximum value of the parameter is a step function of the extreme of motion.

12. The method of implementation 2, 3, 4, and 5, further including:
using the 3D hand model to capture a torsion of the hand during the free-form gestures; and
interpreting the torsion as a parameter of robotic tool actuation.

13. The method of implementation 12, further including:
using the 3D hand model to detect the torsion as an extreme degree of motion of the hand during the free-form gestures; and responsive to the detecting, interpreting a maximum value of a parameter of robotic tool actuation.

14. The method of implementation 13, wherein the maximum value of the parameter is an amplification function of the extreme degree of motion.

15. The method of implementation 13, wherein the maximum value of the parameter is a polynomial function of the extreme of motion.

16. The method of implementation 13, wherein the maximum value of the parameter is a transcendental function of the extreme of motion.

17. The method of implementation 13, wherein the maximum value of the parameter is a step function of the extreme of motion.

18. The method of implementation 2, 3, 4, and 5, further including:
using the 3D hand model to capture a translation of the hand during the free-form gestures; and
interpreting the translation as a parameter of robotic tool actuation.

19. The method of implementation 18, further including:
using the 3D hand model to detect the translation as an extreme degree of motion of the hand during the free-form gestures; and
responsive to the detecting, interpreting a maximum value of a parameter of robotic tool actuation.

20. The method of implementation 19, wherein the maximum value of the parameter is an amplification function of the extreme degree of motion.

21. The method of implementation 19, wherein the maximum value of the parameter is a polynomial function of the extreme of motion.

22. The method of implementation 19, wherein the maximum value of the parameter is a transcendental function of the extreme of motion.

23. The method of implementation 19, wherein the maximum value of the parameter is a step function of the extreme of motion.

24. The method of implementation 2, 3, 4, and 5, further including:
using the 3D hand model to capture a rotation of the hand during the free-form gestures; and
interpreting the rotation as a parameter of robotic tool actuation.

25. The method of implementation 24, further including:
using the 3D hand model to detect the rotation as an extreme degree of motion of the hand during the free-form gestures; and
responsive to the detecting, interpreting a maximum value of a parameter of robotic tool actuation.

26. The method of implementation 25, wherein the maximum value of the parameter is an amplification function of the extreme degree of motion.

27. The method of implementation 25, wherein the maximum value of the parameter is a polynomial function of the extreme of motion.

28. The method of implementation 25, wherein the maximum value of the parameter is a transcendental function of the extreme of motion.

29. The method of implementation 25, wherein the maximum value of the parameter is a step function of the extreme of motion.

30. The method of implementation 2, 3, 4, and 5, further including:
using the 3D hand model to calculate a distance between adjoining base points of fingers of the hand during the free-form gestures; and
interpreting the distance as a parameter of robotic tool actuation.

31. The method of implementation 2, 3, 4, and 5, further including:
using the 3D hand model to calculate a ratio of distance between adjoining base points of fingers of the hand during the free-form gestures to minimal distance between adjoining base points of the fingers; and
interpreting the ratio as a parameter of robotic tool actuation.

32. The method of implementation 2, 3, 4, and 5, further including:
using the 3D hand model to calculate an angle between adjacent fingers of the hand during the free-form gestures; and
interpreting the angle as a parameter of robotic tool actuation.

33. The method of implementation 2, 3, 4, and 5, further including:
using the 3D hand model to calculate a joint angle between adjacent finger segments of the hand during the free-form gestures; and
interpreting the joint angle as a parameter of robotic tool actuation.

34. The method of implementation 2, 3, 4, and 5, further including:
using the 3D hand model to calculate, for the hand, a ratio of fingers' thickness to a maximal finger's thickness; and
interpreting the ratio as a parameter of robotic tool actuation.

35. The method of implementation 2, 3, 4, and 5, further including:
using the 3D hand model to calculate a rate of change of acceleration of the hand during the free-form gestures; and
interpreting the rate as a parameter of robotic tool actuation.

36. The method of implementation 2, 3, 4, and 5, further including:
using the 3D hand model to calculate a velocity of the hand during the free-form gestures; and
interpreting the velocity as a parameter of robotic tool actuation.

37. The method of implementation 2, 3, 4, and 5, further including:
using the 3D hand model to capture an orientation of the hand during the free-form gestures; and
interpreting the orientation as a parameter of robotic tool actuation.

38. The method of implementation 1, further including capturing edge information for fingers of a hand that performs the free-form gestures and computing finger positions for the hand during the free-form gestures.

39. The method of implementation 1, further including capturing edge information for a palm of a hand that performs the free-form gestures and computing palm positions for the hand during the free-form gestures.

40. The method of implementation 1, further including capturing finger segment length information for fingers of a hand that performs the free-form gestures.

41. The method of implementation 1, further including capturing joint angle and segment orientation information of a hand that performs the free-form gestures.

42. The method of implementation 38, 39, 40, and 41, further including:
capturing a curling of the hand during the free-form gestures; and
interpreting the curling as a parameter of robotic tool actuation.

43. The method of implementation 42, further including:
detecting the curling as an extreme degree of motion of the hand during the free-form gestures; and
responsive to the detecting, interpreting a maximum value of a parameter of robotic tool actuation.

44. The method of implementation 43, wherein the maximum value of the parameter is an amplification function of the extreme degree of motion.

45. The method of implementation 43, wherein the maximum value of the parameter is a polynomial function of the extreme of motion.

46. The method of implementation 43, wherein the maximum value of the parameter is a transcendental function of the extreme of motion.

47. The method of implementation 43, wherein the maximum value of the parameter is a step function of the extreme of motion.

48. The method of implementation 38, 39, 40, and 41, further including:
capturing a torsion of the hand during the free-form gestures; and
interpreting the torsion as a parameter of robotic tool actuation.

49. The method of implementation 48, further including:
detecting the torsion as an extreme degree of motion of the hand during the free-form gestures; and
responsive to the detecting, interpreting a maximum value of a parameter of robotic tool actuation.

50. The method of implementation 49, wherein the maximum value of the parameter is an amplification function of the extreme degree of motion.

51. The method of implementation 49, wherein the maximum value of the parameter is a polynomial function of the extreme of motion.

52. The method of implementation 49, wherein the maximum value of the parameter is a transcendental function of the extreme of motion.

53. The method of implementation 49, wherein the maximum value of the parameter is a step function of the extreme of motion.

54. The method of implementation 38, 39, 40, and 41, further including:
capturing a translation of the hand during the free-form gestures; and
interpreting the translation as a parameter of robotic tool actuation.

55. The method of implementation 54, further including:
detecting the translation as an extreme degree of motion of the hand during the free-form gestures; and
responsive to the detecting, interpreting a maximum value of a parameter of robotic tool actuation.

56. The method of implementation 55, wherein the maximum value of the parameter is an amplification function of the extreme degree of motion.

57. The method of implementation 55, wherein the maximum value of the parameter is a polynomial function of the extreme of motion.

58. The method of implementation 55, wherein the maximum value of the parameter is a transcendental function of the extreme of motion.

59. The method of implementation 55, wherein the maximum value of the parameter is a step function of the extreme of motion.

60. The method of implementation 38, 39, 40, and 41, further including:
capturing a rotation of the hand during the free-form gestures; and
interpreting the rotation as a parameter of robotic tool actuation.

61. The method of implementation 60, further including:
detecting the rotation as an extreme degree of motion of the hand during the free-form gestures; and
responsive to the detecting, interpreting a maximum value of a parameter of robotic tool actuation.

62. The method of implementation 61, wherein the maximum value of the parameter is an amplification function of the extreme degree of motion.

63. The method of implementation 61, wherein the maximum value of the parameter is a polynomial function of the extreme of motion.

64. The method of implementation 61, wherein the maximum value of the parameter is a transcendental function of the extreme of motion.

65. The method of implementation 61, wherein the maximum value of the parameter is a step function of the extreme of motion.

66. The method of implementation 38, 39, 40, and 41, further including:
calculating a distance between adjoining base points of fingers of the hand during the free-form gestures; and
interpreting the distance as a parameter of robotic tool actuation.

67. The method of implementation 38, 39, 40, and 41, further including:
calculating a ratio of distance between adjoining base points of fingers of the hand during the free-form gestures to minimal distance between adjoining base points of the fingers; and
interpreting the ratio as a parameter of robotic tool actuation.

68. The method of implementation 38, 39, 40, and 41, further including:
calculating an angle between adjacent fingers of the hand during the free-form gestures; and
interpreting the angle as a parameter of robotic tool actuation.

69. The method of implementation 38, 39, 40, and 41, further including:
calculating a joint angle between adjacent finger segments of the hand during the free-form gestures; and
interpreting the joint angle as a parameter of robotic tool actuation.

70. The method of implementation 38, 39, 40, and 41, further including:
calculating, for the hand, a ratio of fingers' thickness to a maximal finger's thickness; and
interpreting the ratio as a parameter of robotic tool actuation.

71. The method of implementation 38, 39, 40, and 41, further including:
calculating a rate of change of acceleration of the hand during the free-form gestures; and
interpreting the rate as a parameter of robotic tool actuation.

72. The method of implementation 38, 39, 40, and 41, further including:
calculating a velocity of the hand during the free-form gestures; and
interpreting the velocity as a parameter of robotic tool actuation.

73. The method of implementation 38, 39, 40, and 41, further including:
capturing an orientation of the hand during the free-form gestures; and
interpreting the orientation as a parameter of robotic tool actuation.

74. The method of implementation 2, 3, 4, and 5, further including using the 3D model to compute second and third instances of at least one of edge information for fingers, finger positions, palm positions, finger segment length information, and joint angle and segment orientation information.

75. The method of implementation 38, 39, 40, and 41, further including computing second and third instances of at least one of edge information for fingers, finger positions, palm positions, finger segment length information, and joint angle and segment orientation information.

76. The method of implementation 74, further including voting, based on the first, second, and third instances, accepting a majority among the instances as correct.

77. The method of implementation 74, further including voting, based on the first, second, and third instances, accepting an average among the instances as correct.

78. The method of implementation 75, further including voting, based on the first, second, and third instances, accepting a majority among the instances as correct.

79. The method of implementation 75, further including voting, based on the first, second, and third instances, accepting an average among the instances as correct.

80. The method of implementation 1, wherein a parameter of robotic tool actuation is path of the robotic tool during the smoothed emulating motions.

81. The method of implementation 1, wherein a parameter of robotic tool actuation is trajectory of the robotic tool during the smoothed emulating motions.

82. The method of implementation 1, wherein a parameter of robotic tool actuation is velocity of the robotic tool during the smoothed emulating motions.

83. The method of implementation 1, wherein a parameter of robotic tool actuation is angular velocity of the robotic tool during the smoothed emulating motions.

84. The method of implementation 1, wherein a parameter of robotic tool actuation is orientation of the robotic tool during the smoothed emulating motions.

85. The method of implementation 84, wherein a parameter of robotic tool actuation is Euler angles of the robotic tool during the smoothed emulating motions.

86. The method of implementation 84, wherein a parameter of robotic tool actuation include at least one of roll, pitch, and yaw angles of the robotic tool during the smoothed emulating motions.

87. The method of implementation 1, wherein a parameter of robotic tool actuation is temperature applied by the robot tool during the smoothed emulating motions.

88. The method of implementation 1, wherein a parameter of robotic tool actuation is force applied by the robot tool during the smoothed emulating motions.

89. The method of implementation 1, wherein a parameter of robotic tool actuation is torque applied by the robot tool during the smoothed emulating motions.

90. The method of implementation 1, wherein a parameter of robotic tool actuation is at least one of stress, strain, and shear applied by the robot tool during the smoothed emulating motions.

91. The method of implementation 1, further including:
detecting an error in physical arrangement of an environment that includes the workpiece; and
providing the error for human evaluation before producing the smoothed emulating motions.

92. The method of implementation 1, further including automatically providing, to a user performing the free-form gestures, virtual haptographic feedback generated by the smoothed emulating motions, wherein haptographic data used to provide the virtual haptographic feedback is captured by applying sensorized tools to the workpiece.

93. A method of using interaction between free-form gestures and a manipulable object to control interaction of a robotic tool with a workpiece, the method including:
capturing a gesture and interaction of the gesture with a manipulable object in a three-dimensional (3D) sensory space and translating the gesture and the interaction into robotic tool commands that produce smoothed emulating actions performed by a robotic tool on a workpiece.

94. The method of implementation 93, further including:
recognizing a gesture segment within the interaction that represents physical contact between the robotic tool and the workpiece; and
the robotic tool applying a force to the workpiece, wherein a magnitude of the force is based on a parameter of the gesture segment.

95. The method of implementation 93, further including capturing edge information for the manipulable object and computing positions of the manipulable object during the gesture.

96. The method of implementation 95, further including determining a path of the manipulable object during the gesture.

97. The method of implementation 95, further including determining a trajectory of the manipulable object during the gesture.

98. The method of implementation 93, wherein the manipulable object is a real-world object.

99. The method of implementation 93, wherein the manipulable object is a virtual object.

100. The method of implementation 93, wherein the workpiece is a biological tissue or organ.

101. A method of using interaction between free-form gestures and a stationary target object to control interaction of a robotic tool with a workpiece, the method including:
capturing a gesture and interaction of the gesture with a stationary target object in a three-dimensional (3D) sensory space and translating the gesture and the interaction into robotic tool commands that produce smoothed emulating actions performed by a robotic tool on a workpiece.

102. The method of implementation 101, further including:
recognizing a gesture segment within the interaction that represents physical contact between the robotic tool and the workpiece; and
the robotic tool applying a force to the workpiece, wherein a magnitude of the force is based on a parameter of the gesture segment.

103. The method of implementation 101, wherein the stationary target object is a real-world object.

104. The method of implementation 101, wherein the stationary target object is a virtual object.

105. The method of implementation 101, wherein the workpiece is a biological tissue or organ.

106. A method of using free-form gestures to manipulate a robotic tool, the method including:
capturing free-form gestures in a three-dimensional (3D) sensory space and translating the gestures into robotic tool commands that produce smoothed emulating motions by a robotic tool, without literally translating postural information of the gestures into robotic tool commands.

The terms and expressions employed herein are used as terms and expressions of description and not of limitation, and there is no intention, in the use of such terms and expressions, of excluding any equivalents of the features shown and described or portions thereof. In addition, having described certain implementations of the technology disclosed, it will be apparent to those of ordinary skill in the art that other implementations incorporating the concepts disclosed herein can be used without departing from the spirit and scope of the technology disclosed. Accordingly, the described implementations are to be considered in all respects as only illustrative and not restrictive.

What is claimed is:

1. A method of using free-form gestures to manipulate a workpiece by a robotic tool, the method including:
   capturing free-form gestures of a hand in a three-dimensional (3D) sensory space utilizing two cameras to capture sequential images of the hand while empty making motions directed to commanding a robotic tool, analyzing the images as captured and translating the free-form gestures of the hand into robotic tool commands that produce smoothed emulating motions by a robotic tool, including:
      recognizing in the captured images of the hand while empty moving, a gesture segment within the free-form gestures of the hand that represents physical contact between the robotic tool and a workpiece; wherein there is no physical contact between the hand and any object during the gesture segment that represents physical contact;
      determining a command to the robotic tool to apply a force to the workpiece without actual physical contact between the robotic tool and the hand, wherein a magnitude of the force to be applied to the workpiece is determined based on a human hand motion during the gesture segment in which there is no physical contact with the hand as captured by the two cameras, without actual physical contact between the robotic tool and the hand, during the gesture segment associated with a detected path of the hand and a grasping motion of the hand; and
      issuing the command to the robotic tool to apply the force to the workpiece.

2. The method of claim 1, further including capturing edge information for fingers of the hand that performs the free-form gestures and computing finger positions of a 3D solid hand model for the hand during the free-form gestures.

3. The method of claim 1, further including capturing edge information for a palm of the hand that performs the free-form gestures and computing palm positions for a 3D solid hand model for the hand during the free-form gestures.

4. The method of claim 1, further including capturing finger segment length information for fingers of the hand that performs the free-form gestures and initializing a 3D solid hand model for the hand.

5. The method of claim 1, further including capturing joint angle and segment orientation information of the hand that performs the free-form gestures and applying the joint angle and segment orientation information to a 3D solid hand model for the hand during the free-form gestures.

6. The method of claim 2, further including:
   using the 3D solid hand model to capture a curling of the hand during the free-form gestures; and
   interpreting the curling as a parameter of robotic tool translation.

7. The method of claim 6, further including:
   using the 3D solid hand model to detect the curling as an extreme degree of motion of the hand during the free-form gestures; and
   responsive to detecting the curling as an extreme degree of motion of the hand, interpreting a maximum value of a parameter of robotic tool actuation.

8. The method of claim 7, wherein the maximum value of the parameter is an amplification function of the extreme degree of motion.

9. The method of claim 7, wherein the maximum value of the parameter is a polynomial function of the extreme degree of motion.

10. The method of claim 7, wherein the maximum value of the parameter is a transcendental function of the extreme degree of motion.

11. The method of claim 7, wherein the maximum value of the parameter is a step function of the extreme degree of motion.

12. The method of claim 2, further including:
   using the 3D solid hand model to capture a torsion of the hand during the free-form gestures; and
   interpreting the torsion as a parameter of robotic tool actuation.

13. The method of claim 12, further including:
   using the 3D solid hand model to detect the torsion as an extreme degree of motion of the hand during the free-form gestures; and
   responsive to detecting the torsion as the extreme degree of motion, interpreting a maximum value of a parameter of robotic tool actuation.

14. The method of claim 13, wherein the maximum value of the parameter is an amplification function of the extreme degree of motion.

15. The method of claim 13, wherein the maximum value of the parameter is a polynomial function of the extreme degree of motion.

16. The method of claim 13, wherein the maximum value of the parameter is a transcendental function of the extreme degree of motion.

17. The method of claim 13, wherein the maximum value of the parameter is a step function of the extreme degree of motion.

18. The method of claim 2, further including:
   using the 3D solid hand model to capture a translation of the hand during the free-form gestures; and
   interpreting the translation as a parameter of robotic tool actuation.

19. The method of claim 1, further comprising providing to a user haptographic feedback resulting from the performed gestures.

20. A system including one or more processors coupled to memory storing computer instructions to use free-form gestures for manipulating a workpiece by a robotic tool, the computer instructions, when executed on the one or more processors, implement actions comprising:
   capturing free-form gestures of a hand in a three-dimensional (3D) sensory space utilizing two cameras to capture sequential images of the hand while empty making motions directed to commanding a robotic tool, analyzing the images as captured and translating the free-form gestures of the hand into robotic tool commands that produce smoothed emulating motions by a robotic tool, including:
      recognizing in the captured images of the hand while empty moving, a gesture segment within the free-form gestures of the hand that represents physical contact between the robotic tool and a workpiece; wherein there is no physical contact between the hand and any object during the gesture segment that represents physical contact;
      determining a command to the robotic tool to apply a force to the workpiece without actual physical contact between the robotic tool and the hand, wherein a magnitude of the force to be applied to the workpiece is determined based on a human hand motion during the gesture segment in which there is no physical contact with the hand as captured by the two cameras, without actual physical contact between the robotic tool and the hand, during the gesture segment associated with a detected path of the hand and a grasping motion of the hand; and issuing the command to the robotic tool to apply the force to the workpiece.

21. A non-transitory computer readable medium storing a plurality of instructions for programming one or more processors to use free-form gestures for manipulating a workpiece by a robotic tool, the instructions, when executed on the processors, implementing actions including:

capturing free-form gestures of a hand in a three-dimensional (3D) sensory space utilizing two cameras to capture sequential images of the hand while empty making motions directed to commanding a robotic tool, analyzing the images as captured and translating the free-form gestures of the hand into robotic tool commands that produce smoothed emulating motions by a robotic tool, including:

recognizing in the captured images of the hand while empty moving, a gesture segment within the free-form gestures of the hand that represents physical contact between the robotic tool and a workpiece; wherein there is no physical contact between the empty hand and any object during the gesture segment that represents physical contact;

determining a command to the robotic tool to apply a force to the workpiece without actual physical contact between the robotic tool and the hand, wherein a magnitude of the force to be applied to the workpiece is determined based on a human hand motion during the gesture segment in which there is no physical contact with the hand as captured by the two cameras, without actual physical contact between the robotic tool and the hand, during the gesture segment associated with a detected path of the hand and a grasping motion of the hand; and issuing the command to the robotic tool to apply the force to the workpiece.

22. A method of using free-form gestures to manipulate a workpiece by a robotic tool, the method including:

capturing free-form gestures of a hand in a three-dimensional (3D) sensory space while interacting with a manipulable object and translating the free-form gestures made by the hand interacting with the manipulable object into robotic tool commands that produce smoothed emulating motions by a robotic tool, including:

recognizing a gesture segment within the free-form gestures of the hand that represents physical contact between the robotic tool and a workpiece; wherein there is neither physical nor electrical connection facilitating passage of a signal between the manipulable object and the robotic tool and sensor during the gesture segment that represents physical contact;

determining a command to the robotic tool to apply a force to the workpiece without actual physical contact between the robotic tool and the hand, wherein a magnitude of the force to be applied to the workpiece is determined based on a human hand motion captured, without actual physical contact between the robotic tool and the hand and without physical nor electrical connection between the manipulable object and the robotic tool and sensor, during the gesture segment associated with a detected path of the hand and a grasping motion of the hand; and issuing the command to the robotic tool to apply the force to the workpiece.

\* \* \* \* \*